(12) United States Patent
Zhou et al.

(10) Patent No.: US 11,760,707 B2
(45) Date of Patent: Sep. 19, 2023

(54) PROCESS FOR THE SYNTHESIS OF 2,3,3,3-TETRAFLUOROPROPENE

(71) Applicant: Fujian Yongjing Technology Co., Ltd, Shaowu (CN)

(72) Inventors: Changyue Zhou, Shaowu (CN); Yong Wang, Shaowu (CN)

( * ) Notice: Subject to any disclaimer, the term of this patent is extended or adjusted under 35 U.S.C. 154(b) by 2 days.

(21) Appl. No.: 17/095,777

(22) Filed: Nov. 12, 2020

(65) Prior Publication Data
US 2021/0139397 A1    May 13, 2021

(30) Foreign Application Priority Data
Nov. 13, 2019  (DE) .......................... 102019130574.8

(51) Int. Cl.
*C07C 17/281* (2006.01)
*C07C 17/25* (2006.01)
(Continued)

(52) U.S. Cl.
CPC ............. *C07C 17/281* (2013.01); *B01J 23/26* (2013.01); *B01J 27/12* (2013.01); *B01J 31/0239* (2013.01);
(Continued)

(58) Field of Classification Search
CPC .................................................. C07C 17/206
See application file for complete search history.

(56) References Cited

U.S. PATENT DOCUMENTS

| 2,551,571 A | 5/1951 | Culbertson |
| 3,459,818 A | 8/1969 | Michio et al. |

(Continued)

FOREIGN PATENT DOCUMENTS

| CN | 101973842 A | 2/2011 |
| CN | 102491872 A | 6/2012 |

(Continued)

OTHER PUBLICATIONS

Cantillo, D. et al. "Halogenation of organic compounds using continuous flow and microreactor technology" React. Chem. Eng., 2017, 2, 7-19 (Year: 2017).*

(Continued)

*Primary Examiner* — Medhanit W Bahta

(57) ABSTRACT

The present invention pertains to a novel process of manufacturing the compound 2,3,3,3-tetrafluoropropene (1234yf). The compound 1234yf is the newest refrigerant with zero OPD (Ozone Depleting Potential) and zero GWP (Global Warming Potential). Thus, the invention relates to a process, involving a carbene generation route, for the manufacture of the compound 2,3,3,3-tetrafluoropropene (1234yf), of the compound 243db (2,3-dichloro-1,1,1-trifluoropropane), and optionally of the compound 2-chloro-1,1,1-trifluoropropene (1233xf) via carbene route and compound 243db (2,3-dichloro-1,1,1-trifluoropropane). The invention also relates to a process for the manufacture of the compound 2,3,3,3-tetrafluoropropene (1234yf), wherein the compound 243db (2,3-dichloro-1,1,1-trifluoropropane) serves as a starting material, for the manufacture of the compound 2,3,3,3-tetrafluoropropene (1234yf). Further, the invention relates to a process for the manufacture of the compound 2,3,3,3-tetrafluoropropene (1234yf), and of the compound 243db (2,3-dichloro-1,1,1-trifluoropropane), the initial starting materials are selected from the group consisting of com-pound 123 (2,2-dichloro-1,1,1-trifluoroethane), compound 124 (2-chloro-1,1,1,2-tetrafluoroethane), and compound 125 (pentafluoroethane).

4 Claims, 2 Drawing Sheets

(51) Int. Cl.
  *B01J 23/26* (2006.01)
  *B01J 27/12* (2006.01)
  *B01J 31/02* (2006.01)
  *C07C 17/269* (2006.01)

(52) U.S. Cl.
  CPC ............ *C07C 17/25* (2013.01); *C07C 17/269* (2013.01); *B01J 2531/985* (2013.01); *C07C 2523/745* (2013.01); *C07C 2523/843* (2013.01); *C07C 2523/86* (2013.01)

(56) References Cited

U.S. PATENT DOCUMENTS

| | | | |
|---|---|---|---|
| 4,849,554 A | | 7/1989 | Cresswell et al. |
| 5,475,167 A | * | 12/1995 | Nappa ...................... B01J 23/26 |
| | | | 570/166 |
| 5,600,038 A | * | 2/1997 | Wismer ................. B01J 27/125 |
| | | | 510/168 |
| 8,841,493 B2 | | 9/2014 | Guillet et al. |
| 9,018,429 B2 | | 4/2015 | Sedat et al. |
| 2002/0032356 A1 | | 3/2002 | Gelblum et al. |
| 2006/0142622 A1 | | 6/2006 | Gelblum et al. |
| 2007/0197842 A1 | | 8/2007 | Mukhopadhyay et al. |
| 2009/0030247 A1 | | 1/2009 | Johnson et al. |
| 2009/0264689 A1 | | 10/2009 | Rao et al. |
| 2009/0264690 A1 | | 10/2009 | Rao et al. |
| 2010/0305370 A1 | | 12/2010 | Devic et al. |
| 2011/0160499 A1 | * | 6/2011 | Wendlinger .......... C07C 17/206 |
| | | | 570/156 |
| 2011/0190554 A1 | | 8/2011 | Pigamo et al. |
| 2012/0053371 A1 | | 3/2012 | Johnson et al. |
| 2012/0136183 A1 | | 5/2012 | Devic et al. |
| 2012/0267567 A1 | | 10/2012 | Rao et al. |
| 2013/0253235 A1 | | 9/2013 | Johnson et al. |
| 2014/0034870 A1 | | 2/2014 | Rao et al. |
| 2014/0350311 A1 | | 11/2014 | Johnson et al. |
| 2015/0080619 A1 | | 3/2015 | Deur-Bert et al. |
| 2016/0107959 A1 | | 4/2016 | Pigamo et al. |
| 2019/0322917 A1 | | 10/2019 | Rao et al. |

FOREIGN PATENT DOCUMENTS

| | | | | |
|---|---|---|---|---|
| CN | 102516024 A | | 6/2012 | |
| CN | 109438170 A | * | 3/2019 | |
| EP | 939071 B1 | * | 7/2003 | ............ C07C 17/00 |
| GB | 1076699 A | | 7/1967 | |
| WO | WO2017013406 A1 | | 1/2017 | |

OTHER PUBLICATIONS

CN109438170A, machine translation, Mar. 2019, pp. 1-8 (Year: 2019).*

Olah, G. A. et al. "Hydrogen Fluoride-Antimony(V)Fluoride" Apr. 15, 2001, pp. 1-8 (Year: 2001).*

* cited by examiner

PROCESS FOR THE SYNTHESIS OF 2,3,3,3-TETRAFLUOROPROPENE

BACKGROUND OF THE INVENTION

Field of the Disclosure

The invention relates to a process for the manufacture of the compound 2,3,3,3-tetrafluoropropene (1234yf), and of the compound 2,3-dichloro-1,1,1-trifluoropropane (243db). The invention also relates to a process for the manufacture of the compound 2,3,3,3-tetrafluoropropene (1234yf), wherein the compound 2,3-dichloro-1,1,1-trifluoropropane (243db) serves as a starting material. Further, the invention relates to a process for the manufacture of the compound 2,3,3,3-tetrafluoropropene (1234yf), of the compound 2,3-dichloro-1,1,1-trifluoropropane (243db), and optionally of the compound 2-chloro-1,1,1-trifluoropropene (1233xf), wherein the initial starting materials are selected from compound 123(2,2-dichloro-1,1,1-trifluoroethane), from compound 124 (2-chloro-1,1,1,2-tetrafluoroethane), or from compound 125 (pentafluoroethane).

Description of Related Art

The compound 1234yf is the fourth generation refrigerant showing no ODP (Ozone Depleting Potential), and showing a GWP (Global Warming Potential) of less than 1. In comparison the former refrigerant candidate has shown a GWP of 1500.

The only drawback of this fourth generation refrigerant in view of its application is the flammability, like described in a report of Bundesanstaltfür Materialforschung ("Federal Institute of Material Science", Germany): (web.archive.org/web/20120816103321/http://www.umweltbundesamt.de/produkte/dokumente/test_report_hfo1234yf_2010_06.pdf).

The synthesis routes for the compound 2,3,3,3-tetrafluoropropene (1234yf) known in the state of the art performed in liquid phase and gas phase are either giving mixtures, have low conversion rates (energy consuming recycling streams in industrial plant) or are just not practicable in industrial scale due to pure safety and availability of starting materials.

Most common synthesis routes for the compound 2,3,3,3-tetrafluoropropene (1234yf) are the one from Honeywell like described in WO2009/018561 according to Scheme A.

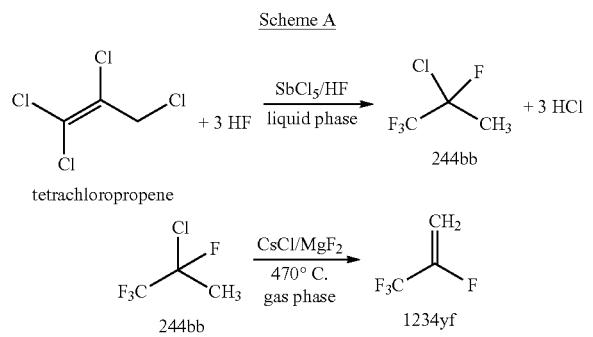

Scheme A

Alone the synthesis of the starting material tetrachloropropene is a four step synthesis out of 1,2,3-trichloropropane (see, e.g., US2007/0197842), which is already a downstream product of allylchloride; see Scheme B.

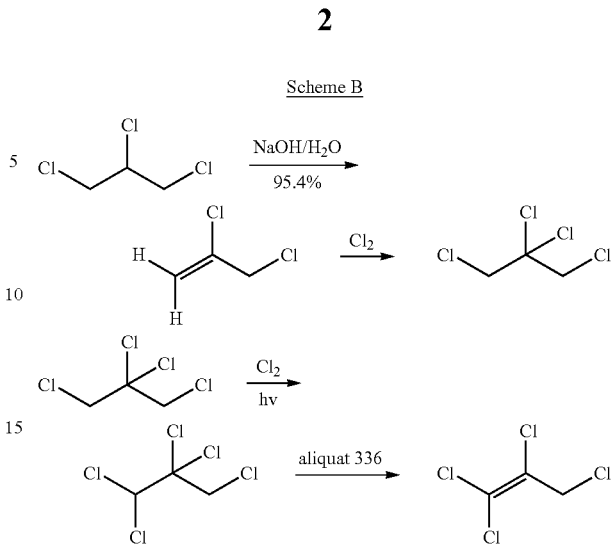

Scheme B

Other routes described in the state of the art, e.g., by Honeywell, are on the same level of complexity like described in WO2008/002499 the synthesis out of 245eb, of 1234yf and the isomers 1234ze (on the market as "Solstice"); see Scheme C.

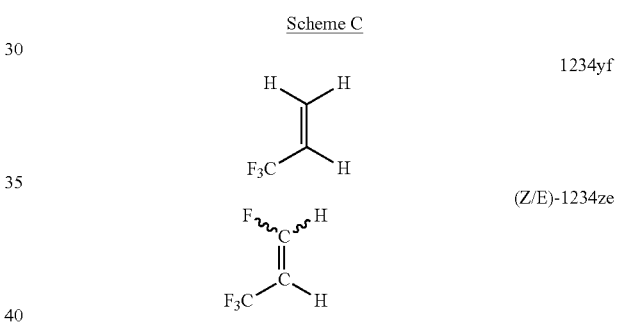

Scheme C

The compound HFC 245eb can be prepared by the hydrogenation of $CF_3CClFCCl_2F$ (CFC-215bb) over a palladium on carbon catalyst as disclosed in WO 2008/002501 A2, and which is incorporated herein by reference in its entirety, or by the hydrogenation of $CF_3CF=CFH$ as disclosed by Du Pont in WO 2008/002499; see Scheme D.

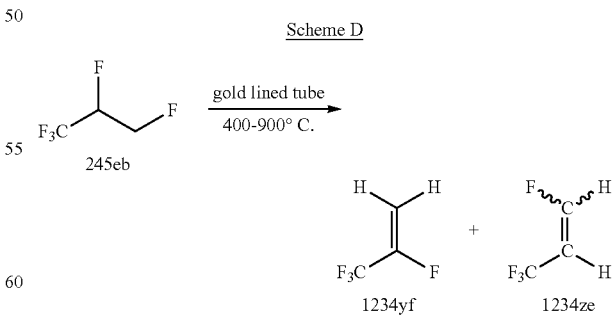

Scheme D

In US 2005/0245773 Honeywell is disclosing a three-step process to produce 1,1,1,3-tetrafluoropropene (1234ze isomeric mixture) but this 1234 isomer seems to have some lower market importance; see Scheme E.

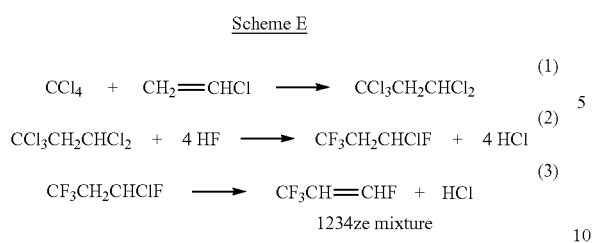

Scheme E $$CCl_4 + CH_2=CHCl \longrightarrow CCl_3CH_2CHCl_2 \quad (1)$$
$$CCl_3CH_2CHCl_2 + 4\,HF \longrightarrow CF_3CH_2CHClF + 4\,HCl \quad (2)$$
$$CF_3CH_2CHClF \longrightarrow CF_3CH=CHF + HCl \quad (3)$$

1234ze mixture

Furthermore, Archema describes the synthesis of 2,3,3,3-tetrafluoropropene (1234yf) in WO2013/114015 (corresponding to US2015/0080619) out of chlorinated propanes like pentachloropropanes in gas phase over chromium catalyst; as shown for example in Scheme F.

In an alternative synthesis route of Archema, the synthesis starts from HFP, and is described, for example, in WO 2010/029240, WO 2009/118632, US 2012/0136183, U.S. Pat. No. 8,841,493, and in U.S. Pat. No. 9,018,429; as shown for example in Scheme G.

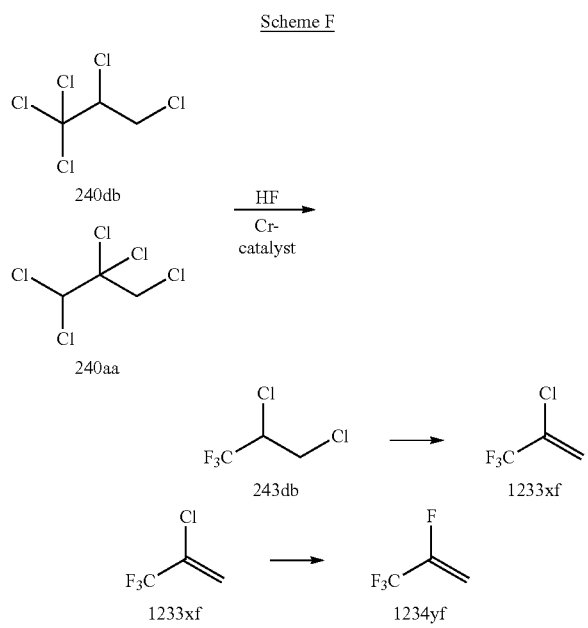

Scheme F

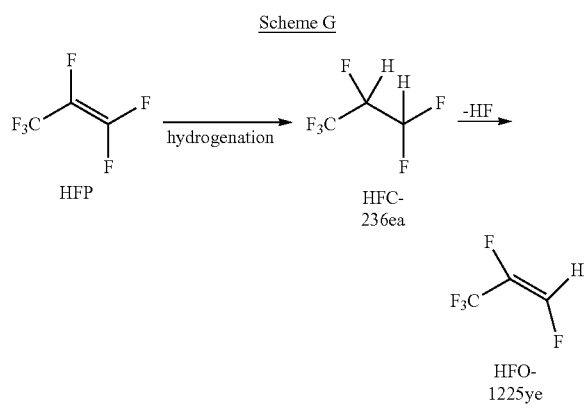

Scheme G

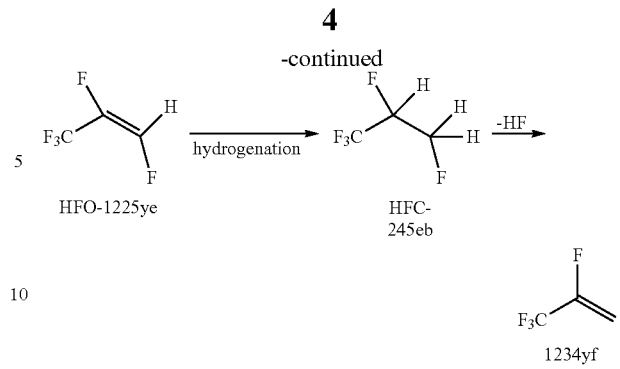

Furthermore, the synthesis of 243db, and of 1233xf out of 243db, is known from WO 2017/013406, but 243db is prepared out of expensive trifluoropropene.

In general the generation of dihalogenatedcarbenes, e.g., out of $CF_2ClH$ (HCFC 22) for production of tetrafluoroethylene (TFE) is well known and practiced in very large industrial scale. Also the generation of difluorocarbene out of halogenodifluoro acetates is known, but less relevant for production of high volume materials like refrigerants. TFE improvements are described by Dae Jin Sung, Dong Ju Moon, Yong Jun Lee, Suk-In Hong: *Catalytic Pyrolysis of Difluorochloromethane to Produce Tetrafluoroethylene. In: International Journal of Chemical Reactor Engineering.* 2, 2004, doi:10.2202/1542-6580.1065 and in CN 101973842, CN 102516024 and CN 102491872. First applications also linked to TFE were disclosed, e.g., in 1962 by Farbwerke Hoechst in DE 1217946, where compound HCFC 22 is pyrolyzed in presence of overheated water vapor, Asahi Glass U.S. Pat. No. 3,459,818, and also combined production of TFE and HFP as in ICI's patent EP 0287219.

An improved industrially feasible process is described by DuPont in WO 02/06193 using gold lined equipment and improved parameters which reduces undesired by-product formation and enhances productivity, e.g., necessitating less cleaning from polymerized side product materials. U.S. Pat. No. 2,551,571 also filed by Du Pont discloses already similar effects by using a silver tube. Recent investigations made by University Bayreuth describe the preparation of different fluoroolefins in SiC microreactors (www.dbu.de/OPAC/ab/DBU-Abschlussbericht-AZ-31819.pdf). These newest results were presented in a Poster on Dechema "JahrestreffenReaktionstechnik" 2018 in Wrzburg und des "22nd International Symposium on Fluorine" in Oxford.

OBJECTS OF THE INVENTION

It is an object of the present invention to provide a high efficient process for the manufacture of the compound 2,3,3,3-tetrafluoropropene (1234yf), of the compound 2,3-dichloro-1,1,1-trifluoropropane (243db), and optionally of the compound 2-chloro-1,1,1-trifluoropropene (1233xf).

It is preferably an object of the present invention to provide a high efficient process for the manufacture of the compound 2,3,3,3-tetrafluoropropene (1234yf), and wherein the compound of the compound 2,3-dichloro-1,1,1-trifluoropropane (243db) serves as a starting material in the process for the manufacture of the compound 2,3,3,3-tetrafluoropropene (1234yf).

It is another object of the present invention to provide a high efficient process for the manufacture of the compound 243db (2,3-dichloro-1,1,1-trifluoropropane).

It is preferably still another object of the present invention to provide a high efficient process for the manufacture of the compound 2,3,3,3-tetrafluoropropene (1234yf), and wherein the compound 243db (2,3-dichloro-1,1,1-trifluoropropane) serves as a starting material in the process for the manufacture of the compound 2,3,3,3-tetrafluoropropene (1234yf).

It is still another object of the present invention to provide a high efficient process for the manufacture of the compound 2,3,3,3-tetrafluoropropene (1234yf), and wherein the initial starting material is a compound selected from the group consisting of compound 123 (2,2-dichloro-1,1,1-trifluoroethane), compound 124 (2-chloro-1,1,1,2-tetrafluoroethane), and compound 125 (pentafluoroethane), and can serve as a starting material in the process for the manufacture of the compound 2,3,3,3-tetrafluoropropene (1234yf). Herein, preferably it is an object of the present invention that the compound 123 (2,2-dichloro-1,1,1-trifluoroethane can serve as the initial starting material in the process for the manufacture of the compound 2,3,3,3-tetrafluoropropene (1234yf).

SUMMARY OF THE INVENTION

The objects of the invention are solved as defined in the claims, and described herein after in detail. In particular, the present invention pertains to a novel process, in particular, of manufacturing the compound 2,3,3,3-tetrafluoropropene (1234yf), and of the compound 2,3-dichloro-1,1,1-trifluoropropane (243db). The compound 1234yf is the newest refrigerant with zero OPD (Ozone Depleting Potential) and zero GWP (Global Warming Potential). Herein, the processes of the present invention have in common that the manufacture of the compounds involve at least one carbene generation step.

In chemistry, a carbene is a molecule containing a neutral carbon atom with a valence of two and two unshared valence electrons. The general formula is R—C(:)—R' or R=C(:) where the R and R' represent organic carbon substituents or hydrogen atoms, and (:) represents two unshared valence electrons of the carbon atom (C).

In the context of the present invention, a carbene of interest in the processes of manufacturing compounds according to the objects of the invention, is generated out of a trifluoroethane compound of the formula $CF_3$—$CHX_nY_{2-n}$, wherein X and Y, each independently denotes a halogen atom selected from the group consisting of fluorine (F) and chlorine (Cl); n is an integer of 1 or 2. The preferred a halogen atom of the group of fluorine (F) and chlorine (Cl) is chlorine (Cl), for example, trifluoromethyl chloride.

The preferred starting compounds for generating a carbene of interest in the processes of manufacturing compounds according to the objects of the invention, having a formula $CF_3$—C(:)X, is a trifluoroethane compound of the formula $CF_3$—$CHX_nY_{2-n}$, selected from the group consisting of compound 123 (2,2-dichloro-1,1,1-trifluoroethane), compound 124 (2-chloro-1,1,1,2-tetrafluoroethane), and compound 125 (pentafluoroethane).

The said carbene of interest in the processes of manufacturing compounds according to the objects of the invention, having the said formula $CF_3$—C(:)X, is reacted with a methyl halogenide compound of formula $CH_3X$, wherein X denotes a halogen atom selected from the group consisting of fluorine (F), chlorine (Cl), bromine (Br), and iodine (J). The preferred a halogen atom is, however, selected from the group consisting of fluorine (F) and chlorine (Cl).

Although, a methyl halogenide compound of the formula $CH_3X$, wherein X denotes a halogen atom from the group of bromine (Br) and iodine (J), may be employed, for example, methyl bromide ($CH_3Br$) or methyl iodide ($CH_3I$), this variant of the invention presently is economically less feasible, than variant of the invention variant of the invention employing a methyl halogenide compound of the formula $CH_3X$, wherein X denotes a halogen atom from the preferred group of fluorine (F) and chlorine (Cl), for example, preferably methyl chloride ($CH_3Cl$).

In this context of manufacturing compounds by a process involving at least one carbene generation step, the present invention pertains to a novel process, in particular, of manufacturing the compound 2,3,3,3-tetrafluoropropene (1234yf), and of the compound 2,3-dichloro-1,1,1-trifluoropropane (243db). The invention also relates to a process for the manufacture of the compound 2,3,3,3-tetrafluoropropene (1234yf), wherein the compound 243db(2,3-dichloro-1,1,1-trifluoropropane)serves as a starting material, for the manufacture of the compound 2,3,3,3-tetrafluoropropene (1234yf).

Further, the invention relates to a process for the manufacture of the compound 2,3,3,3-tetrafluoropropene (1234yf), of the compound 2,3-dichloro-1,1,1-trifluoropropane (243db), and optionally of the compound 2-chloro-1,1,1-trifluoropropene (1233xf), wherein the initial starting materials are selected from compound 123 (2,2-dichloro-1,1,1-trifluoroethane), from compound 124 (2-chloro-1,1,1,2-tetrafluoroethane), or from compound 125 (pentafluoroethane).

Further, the invention relates to a process for the manufacture of the compound 2,3,3,3-tetrafluoropropene (1234yf), of the compound 2,3-dichloro-1,1,1-trifluoropropane (243db),and optionally of the compound 2-chloro-1,1,1-trifluoropropene (1233xf), wherein the initial starting materials are selected from the group consisting of compound 123 (2,2-dichloro-1,1,1-trifluoroethane), compound 124 (2-chloro-1,1,1,2-tetrafluoroethane), and compound 125 (pentafluoroethane). The compound 123 (2,2-dichloro-1,1,1-trifluoroethane is preferred as the initial starting material. In particular, the process of the invention involves a carbene generation step, and wherein the carbene formed is further reacted towards the said targeted compounds of the invention, especially finally towards the compound 2,3,3,3-tetrafluoropropene (1234yf).For example, the chemistry to produce compound 243db is shown in Step 1 (Carbene Reaction) of Scheme 1 further below in the Detailed Description of the Invention. For example, the chemistry to produce compound 1234yf out of compound 243db is shown in Step 2 (Addition/Elimination Reaction) of Scheme 1 further below in the Detailed Description of the Invention.

DESCRIPTION OF THE PREFERRED EMBODIMENTS

Definitions

Figure 1:
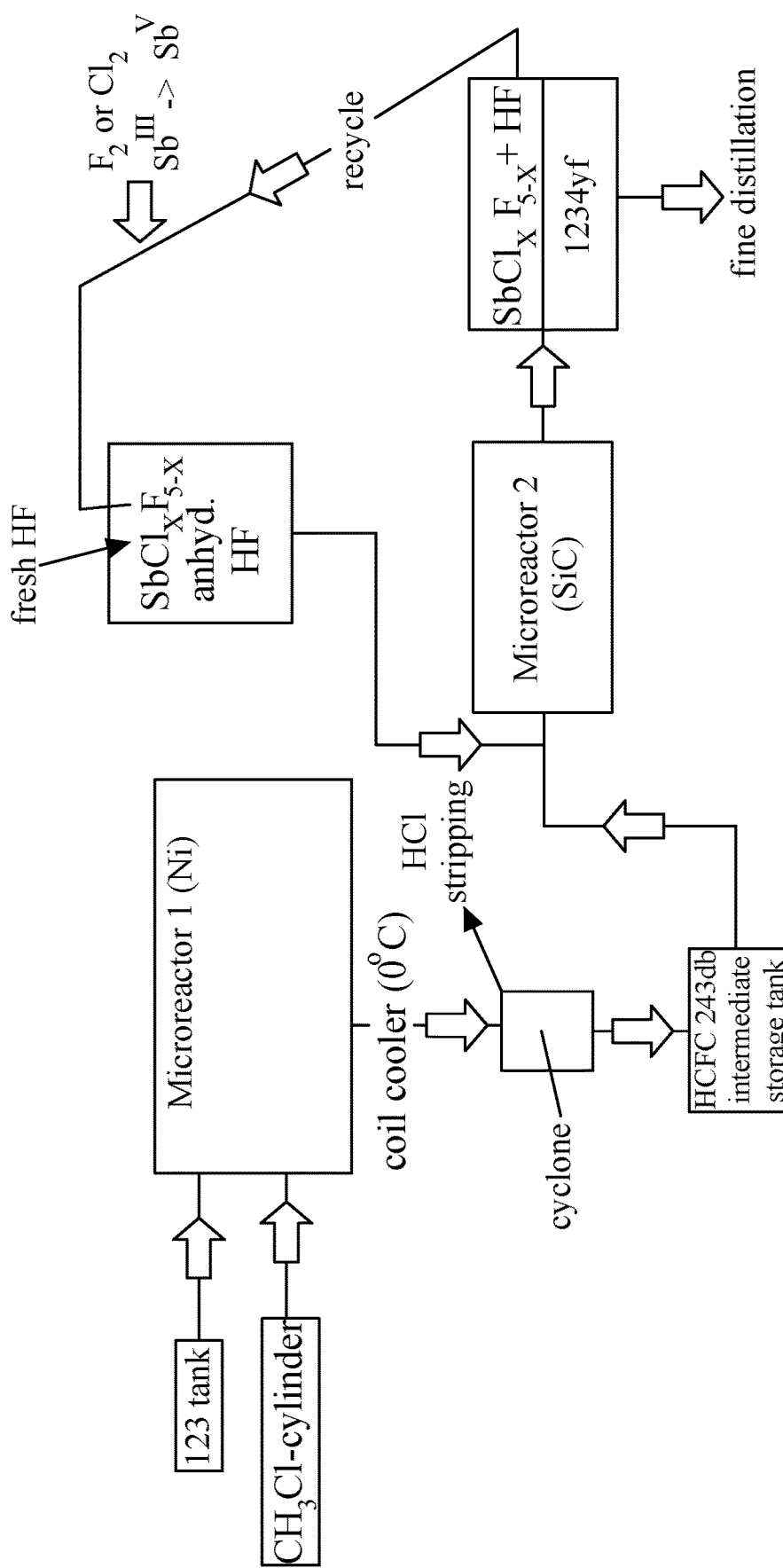
FIG. 1 shows an example embodiment of the process according to the invention and the synthesis of the compound 1234yf out of the compound 123 as the initial starting material, and performed as a reaction sequence in two microreactors.

Compounds in the context of the invention: The compound "1234yf" is 2,3,3,3-tetrafluoropropene. The compound "243db" is 2,3-dichloro-1,1,1-trifluoropropane. The compound "123" or "HCFC 123" is 2,2-dichloro-1,1,1-trifluoroethane. The compound "124" is 2-chloro-1,1,1,2-tetrafluoroethane. The compound "125" is pentafluoroethane. The compound "1233xf" is 2-chloro-1,1,1-trifluoropropene. The compound "244bb" is 2-chloro-1,1,1,2-tetrafluoropropane.

The term "liquid medium" or "liquid phase" may mean a solvent which inert to fluorination under the reaction conditions of the direct fluorination, in which the starting compound and/or fluorinated target compound may be dissolved, and/or the starting compound itself may be a liquid serving itself as liquid medium or liquid phase, and in which the fluorinated target compound may be dissolved if it is not a liquid, or if it is a liquid may also serve as the liquid medium or liquid phase.

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

The term "vol.-%" as used herein means "% by volume".

The term "wt.-%" as used herein means "% by weight". Unless otherwise stated, all percentages (%) as used herein denote "wt.-%" or "% by weight", respectively.

Any pressure value or range of pressure values given herein in, i.e., "bar", unless otherwise stated refer to "bar absolute" (abs.).

The numerical ranges disclosed herein include all values from, and including, the lower and upper value. For ranges containing explicit values (e.g., 1 to 7), any subrange between any two explicit values is included (e.g., 1 to 2; 2 to 6; 5 to 7; 3 to 7; 5 to 6; etc.).

The term "tube-like" is synonymous to the term "pipe-like" and vice versa.

As briefly described in the Summary of the Invention, and defined in the claims and further detailed by the following description and examples herein, the invention is particularly directed to processes of manufacturing the compound 2,3,3,3-tetrafluoropropene (1234yf), which is the newest refrigerant with zero OPD (Ozone Depleting Potential) and zero GWP (Global Warming Potential), and of further compounds such as the compound 2,3-dichloro-1,1,1-trifluoropropane(243db), which can serve as a starting material in the manufacture of the compound 2,3,3,3-tetrafluoropropene (1234yf), and optionally of the compound 2-chloro-1,1,1-trifluoropropene (1233xf); and wherein the processes of the present invention have in common that the manufacture of the compounds involve at least one carbene generation step, e.g., as described in the Summary of the Invention above.

Thus, the invention in particular relates to a process for the manufacture of the compound 2,3,3,3-tetrafluoropropene (1234yf), and of the compound 2,3-dichloro-1,1,1-trifluoropropane (243db). The invention also relates to a process for the manufacture of the compound 2,3,3,3-tetrafluoropropene (1234yf), wherein the compound 2,3-dichloro-1,1,1-trifluoropropane (243db) serves as a starting material. Further, the invention relates to a process for the manufacture of the compound 2,3,3,3-tetrafluoropropene (1234yf), of the compound 2,3-dichloro-1,1,1-trifluoropropane (243db), and optionally of the compound 2-chloro-1,1,1-trifluoropropene (1233xf), wherein the initial starting materials are selected from the group consisting of compound 123 (2,2-dichloro-1,1,1-trifluoroethane), compound 124 (2-chloro-1,1,1,2-tetrafluoroethane), and compound 125 (pentafluoroethane). The compound 123 (2,2-dichloro-1,1,1-trifluoroethane is preferred as the initial starting material. In particular, the process of the invention involves a carbene generation step, and wherein the carbene formed is further reacted towards the targeted compounds of the invention, especially finally towards the compound 2,3,3,3-tetrafluoropropene (1234yf).

The present invention pertaining in particular to a novel process of manufacturing the compound 2,3,3,3-tetrafluoropropene(1234yf), which is the newest refrigerant with zero OPD (Ozone Depleting Potential) and zero GWP (Global Warming Potential), shall be described and exemplified in more detail hereinafter, e.g., by reference to, but not being limited to, preferred embodiments of the invention.

New Process for the Synthesis of 1234yf:

According to the present invention it now was found, for example, that $CF_3$—$CHCl_2$ (HCFC123) can be conveniently reacted to the compound 243db in high yields with $CH_3Cl$ in a carbene reaction in a first step. The chemistry to compound 243db is according to the reaction step 1 in Scheme 1 below, which is a carbene reaction step.

The compound 243db resulting from the first step, then in a second step is further reacted to yield the compound 1234yf. The chemistry starting from compound 243db to provide the compound 1234yf is according reaction step 2 in Scheme 1 below, which is an addition/elimination reaction step.

The novel process of manufacturing the compound 2,3,3,3-tetrafluoropropene (1234yf) according to the present invention is a two-step process involving in a first step a carbene reaction, starting from HCFC 123 (2,2-dichloro-1,1,1-trifluoroethane) as starting compound in the first step, and reacting the carbene compound formed, e.g., formed in situ, as exemplified with methyl chloride ($CH_3Cl$) and elimination of HCl (hydrogen chloride), to produce the compound 2,3-dichloro-1,1,1-trifluoropropane (243db) as the reaction product of the first step. Note: The invention is exemplified with methyl chloride ($CH_3Cl$), but can analogously, for example, be also performed with any other methyl halogenide compound of the formula $CH_3X$, as defined above in the Summary of the Invention.

The compound 2,3-dichloro-1,1,1-trifluoropropane (243db) may either subsequently, e.g., without or with intermediate purification, stored in an intermediate storage tank, or directly be further reacted in the second step of the process to produce the compound 2,3,3,3-tetrafluoropropene (1234yf), or optionally to produce the compound 1233xf (2-chloro-1,1,1-trifluoropropene), or if desired, may be isolated and/or purified, e.g., as product on its own or for different purpose or application.

The carbene reaction in the first process step of manufacturing the compound 2,3,3,3-tetrafluoropropene (1234yf) according to the present invention can be performed by two methods, as exemplified with methyl chloride ($CH_3Cl$):

Method 1A: Carbene generation in liquid phase with phase transfer catalyst and base, and reaction with methyl chloride ($CH_3Cl$) and elimination of HCl (hydrogen chloride); or Method 1B: Carbene generation in gas phase, high temperature thermolysis, and reaction with methyl chloride ($CH_3Cl$) and elimination of HCl (hydrogen chloride).

The said carbene reaction in the said first process step of invention is exemplified with methyl chloride ($CH_3Cl$), but can analogously, for example, be also performed with any other methyl halogenide compound of the formula $CH_3X$, as defined above in the Summary of the Invention.

In the second step the compound 2,3-dichloro-1,1,1-trifluoropropane (243db) formed in the carbene reaction of the first step, then is reacted involving an addition reaction of HF (hydrogen fluoride) and elimination of HCl (hydrogen chloride), to produce the compound 2,3,3,3-tetrafluoropropene (1234yf), or optionally to produce the compound the compound 1233xf (2-chloro-1,1,1-trifluoropropene).

The addition reaction in the second process step of manufacturing the compound 2,3,3,3-tetrafluoropropene (1234yf) according to the present invention can be performed by two methods:

Method 2A: Addition reaction of HF (hydrogen fluoride) and elimination of HCl (hydrogen chloride), both in liquid phase, and induced by Lewis acid; or Method 2B: Addition reaction of HF (hydrogen fluoride) and elimination of HCl (hydrogen chloride), both in gas phase in the presence of a, fluorination and/or halogenation, catalyst.

The novel process of manufacturing the compound 2,3,3,3-tetrafluoropropene (1234yf) according to the present invention is a two-step process, for example, which is shown in the following Scheme 1.

Scheme 1

Step 1 (Carbene Reaction)

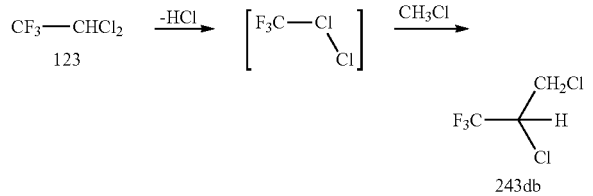

Step 2 (Addition/Elimination Reaction)

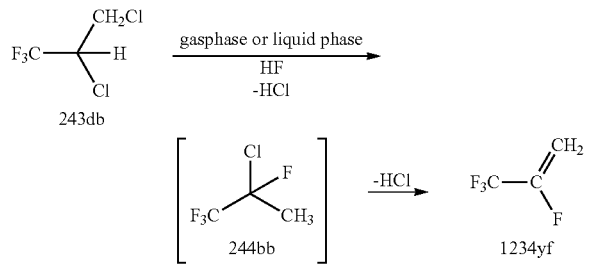

The process of the invention, alternatively to starting from compound 123, can also be performed, starting from the compound 124 (2-chloro-1,1,1,2-tetrafluoroethane) or the compound 125 (pentafluoroethane), and is also involving the carbene generation in the first step of the process according to the present invention.

The compound 124 (chlorotetrafluoroethane) converted under the inventive conditions gave 1234yf directly but 124 as starting material is less conveniently available in large industrial scale. See Scheme 2.

Scheme 2

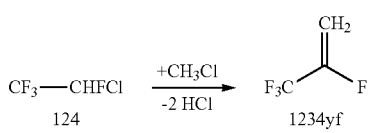

But the compound 125 is produced in large industrial scale and conveniently available, e.g., by the reaction as shown in Scheme 3.

Scheme 3

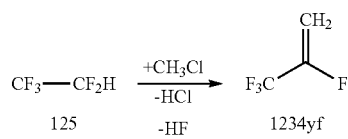

The reaction starting from 124 and also 125 proceeded in a Ni-tube reactor heated to 850° C. but conversion rates with 125 were around 50% lower (carbene generation) rate compared to 123 as starting material. In principle, but not economic feasible—due to needed deep temperatures—is the preparation of the suitable precursors $CF_3$—CF:—carbene out of 125 or $CF_3$—CCl:—carbene out of 124 over the corresponding Lithium salts which preparation is described by Kazakova, Olesya; Roeschenthaler, Gerd-Volker in "Efficient Preparations of Fluorine Compounds" (2013), 205-209, but never used for 1234yf preparation, mentioned here for (scientific) complete information reason only.

However, as compared to the processes shown in Scheme 2 (for compound 124 as initial starting material) and in Scheme 3 (for compound 125, preferred over compound 124, as initial starting material), the process of the invention, starting from compound 123 (2,2-dichloro-1,1,1-trifluoroethane), and involving the carbene generation in the first step of the process according to the present invention, is particularly preferred. See Scheme 1 above.

New process for the synthesis of 1233xf:

According to the present invention it was also found that $CF_3$—$CHCl_2$ (HCFC 123) can be conveniently reacted to the compound 1233xf in high yields with $CH_3Cl$ involving a carbene reaction in a first step, as described above, and also applicable in context of producing the compound 1233xf. For example, in a simple tube reactor, the reaction cannot be stopped at compound 243db stage, and 2 mol equivalents of HCl are eliminated. The chemistry to compound 1233xf is according to the reaction step 1 in Scheme 4 below.

The compound 1233xf resulting from the first step, then in a second step is further reacted to yield the compound 1234yf. The chemistry starting from compound 1233xf to compound 1233xf to provide the compound 1234yf is according reaction step 2 in Scheme 4 below.

This process of manufacturing the compound 2,3,3,3-tetrafluoropropene (1234yf) via the compound 1233xf, is also a two-step process involving in a first step a carbene reaction according to the invention, as described above in the Summary of the Invention, starting from, e.g., HCFC 123 (2,2-dichloro-1,1,1-trifluoroethane) as starting compound in the first step, and reacting the carbene compound formed, e.g., formed in situ, for example, with methyl chloride ($CH_3Cl$) and elimination of HCl (hydrogen chloride), to produce the compound 1233xf (2-chloro-1,1,1-trifluoropropene) as the reaction product of the first step.

The compound 1233xf (2-chloro-1,1,1-trifluoropropene) may either subsequently, e.g., without or with intermediate purification, stored in an intermediate storage tank, or directly be further reacted in the second step of the process to produce the compound 2,3,3,3-tetrafluoropropene (1234yf), or, if desired, the compound 1233xf (2-chloro-1,1,1-trifluoropropene) may be isolated and/or purified, e.g., as product on its own or for different purpose or application.

Scheme 4

Step 1 (Carbene Reaction)

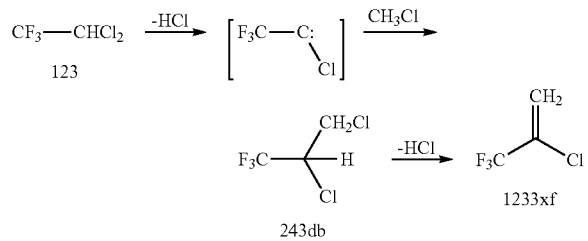

Step 2 (Addition/Elimination Reaction)

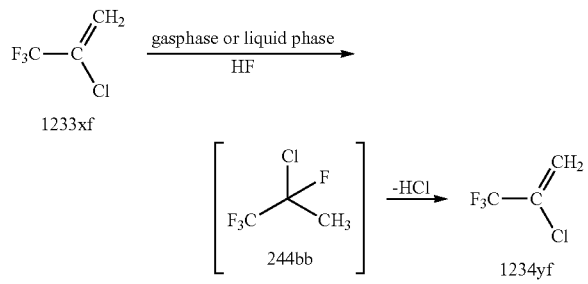

Accordingly, the invention may also relate to a novel process of manufacturing the compound 2-chloro-1,1,1-trifluoropropene(1233xf), involving a carbene reaction step according to the present invention, for example, via the intermediate, or in particular in situ, compound 243db, for example, via the carbene route in a process which is shown in the following Scheme 5.

Scheme 5

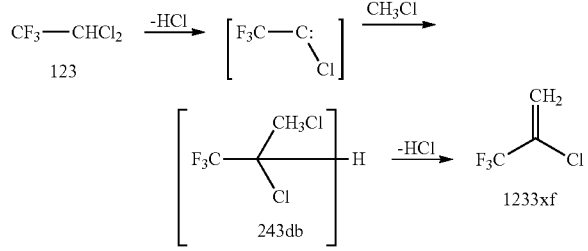

Method 1A and 1B (Carbene Generation):

In chemistry, a carbene is a molecule containing a neutral carbon atom with a valence of two and two unshared valence electrons. The general formula is R—C(:)—R' or R=C(:) where the R and R' represent organic carbon substituents or hydrogen atoms, and (:) represents two unshared valence electrons of the carbon atom (C). Reference is made to the Summary of the Invention, and the carbene generation step, e.g., as described therein, and as applicable in the context of the processes of the invention, and which here shall be further detailed for the purpose of the invention.

Generation of carbenes can be achieved by several methods known in the state of the art. In the context of the present invention, as indicated herein above, the carbene compound is either generated in liquid phase with phase transfer catalyst and base (Method 1A), or the carbene compound is generated in gas phase by high temperature thermolysis (Method 13).

Carbenes are reactive and usually formed as intermediates only, and thus react further with suitable reactant compounds, e.g., in context of the present invention the reactant compound is, for example, methyl chloride ($CH_3Cl$). The said carbene reaction in the said first process step of invention is exemplified with methyl chloride ($CH_3Cl$), but can analogously, for example, be also performed with any other methyl halogenide compound of the formula $CH_3X$, as defined above in the Summary of the Invention.

Method 1A:

Carbene generation in liquid phase with phase transfer catalyst and base.

In the context of the present invention the carbene compound is formed, in a method 1A, by base-induced elimination HX from haloforms (R—$CHX_2$, wherein X denotes a halogen, e.g. especially chlorine, Cl) under phase-transfer conditions, e.g., using a PTC (phase-transfer catalyst).

The haloform employed in context of the present invention for generating a carbene of interest in the processes of manufacturing compounds according to the objects of the invention, is a trifluoroethane compound of the formula $CF_3$—$CHX_nY_{2-n}$, as defined above in the Summary of the Invention, for example, but not limited to, trifluoromethyl chloride.

In chemistry, a phase-transfer catalyst or PTC is a catalyst that facilitates the migration of a reactant from one phase into another phase where reaction occurs. Phase-transfer catalysis is a special form of heterogeneous catalysis. Ionic reactants are often soluble in an aqueous phase but insoluble in an organic phase in the absence of the phase-transfer catalyst. The catalyst functions like a detergent for solubilizing the salts into the organic phase. Phase-transfer catalysis refers to the acceleration of the reaction upon the addition of the phase-transfer catalyst.

By using a PTC process, one can achieve faster reactions, obtain higher conversions or yields, make fewer by-products, eliminate the need for expensive or dangerous solvents that will dissolve all the reactants in a single phase, eliminate the need for expensive raw materials and/or minimize waste problems. Phase-transfer catalysts are especially useful in green chemistry, by allowing the use of water, the need for organic solvents is reduced.

Contrary to common perception, PTC is not limited to systems with hydrophilic and hydrophobic reactants. PTC is sometimes employed in liquid/solid and liquid/gas reactions. As the name implies, one or more of the reactants are transported into a second phase which contains both reactants.

In the state of the art, several types of PTC process are known. For example, phase-transfer catalysts for anionic reactants are often quaternary ammonium salts. Commercially important phase-transfer catalysts include, for example, but are not limited to, benzyltriethylammonium chloride, methyltricaprylammonium chloride, methyltributylammonium chloride, and methyltrioctylammonium chloride. Organic phosphonium salts are also used for example, but are not limited to, hexadecyltributylphosphonium bromide. The phosphonium salts tolerate higher temperatures, but may be unstable toward base, then degrading to phosphine oxide.

It was demonstrated that many carbene reactions can be performed rapidly at around room temperature using catalysts such as tetra-n-butylammonium bromide and methyltrioctylammonium chloride in benzene/water systems.

An alternative to the use of "quaternary salts" is to convert alkali metal cations into hydrophobic cations. In the research lab, crown ethers are used for this purpose. Polyethylene glycols are more commonly used in practical applications. These ligands encapsulate alkali metal cations (typically $Na^+$ and $K^+$), affording large lipophilic cations. These polyethers have a hydrophilic "interiors" containing the ion and a hydrophobic "exterior".

According to the present invention the carbene generation is performed in liquid phase with phase transfer catalyst and base. For general information see M. Makosza, Pure Appl. Chem., Vol. 72, No. 7, pp. 1399-1403, 2000.

The phase transfer catalyst may comprise a compound of at least one of the compound classes of, for example: a) linear or cyclic ammonium salts, b) heterocyclic ammonium salts, c) non-ionic phase transfer compounds, d) phosphonium salts, and combinations thereof. Examples, but not intended to be limited thereto, are for the said compound classes are:

a) Ammonium salts like: benzalkoniumchloride (CAS Number: 63449-41-2), benzyldimethylhexylammonium chloride (CAS Number: 22559-57-5), 2-bromoethyl)trimethylammonium bromide(CAS Number: 2758-06-7), hexyltrimethylammonium bromide, (CAS Number: 2650-53-5), and tetrabutylammonium bromide (CAS Number: 1643-19-2); and the commercially phase-transfer catalysts already mentioned above, for example, including benzyltriethylammonium chloride, methyltricaprylammonium chloride, methyltributylammonium chloride, and methyltrioctylammonium chloride.

b) Heterocyclic ammonium salts like: 1-butyl-2,3-dimethylimidazolium chloride (CAS Number: 98892-75-2), hexadecylpyridinium bromide (CAS Number: 140-72-7), and 1-methylimidazolium hydrogen sulfate (CAS Number: 681281-87-8);

c) Non-ionic phase transfer compounds: like DL-α-tocopherol methoxypolyethylene glycol succinate (CAS Number: 1309573-60-1); and d) Phosphonium salts like: tetrabutylphosphonium bromide (CAS Number: 3115-68-2), methyltriphenoxyphosphonium iodide (CAS Number: 17579-99-6), tetrabutylphosphoniummethanesulfonate (CAS Number: 98342-59-7), tetraphenylphosphonium bromide (CAS Number: 2751-90-8), trihexyltetradecylphosphonium bromide (CAS Number: 654057-97-3), and trihexyltetradecylphosphonium chloride (CAS Number: 258864-54-9); and hexadecyltributylphosphonium bromide, a commercially phase-transfer catalysts already mentioned above.

The liquid phase may comprise as a solvent, e.g., any inert solvent or combinations thereof. Examples, but not intended to be limited thereto, including mixtures of solvents are, e.g., trichloromethyl toluene, $CH_2Cl_2$ (methylene dichloride), toluene, DMF, DMSO, ethylene glycol, water ($H_2O$), butyrolactone. As accelerator, some crown ether can be added as well, e.g., such crown ethers as known to the person skilled in the art.

In chemistry, a base is, for example, (i) an inorganic substance that can accept hydrogen ions (protons, $H^+$). Such a base may be an inorganic substance, including but not limited to, KOH, NaOH, LiOH, $Ca(OH)_2$, or combinations thereof. Hence, in chemistry, bases (i) are substances that, in aqueous solution, release hydroxide ($OH^-$) ions, are slippery to the touch, can taste bitter if an alkali, change the color of indicators (e.g., turn red litmus paper blue), react with acids to form salts, promote certain chemical reactions (base catalysis), accept protons ($H^+$) from any proton donor or contain completely or partially displaceable $OH^-$ ions. Examples of bases are the hydroxides of the alkali metals and the alkaline earth metals (NaOH, $Ca(OH)_2$, etc.; see alkali hydroxide and alkaline earth hydroxide). In water, by altering the autoionization equilibrium, bases yield solutions in which the hydrogen ion activity is lower than it is in pure water, i.e., the water has a pH higher than 7.0 at standard conditions. A soluble base is called an alkali if it contains and releases $OH^-$ ions quantitatively. However, it is important to realize that basicity is not the same as alkalinity. Metal oxides, hydroxides, and especially alkoxids are basic, and conjugate bases of weak acids are weak bases.

In chemistry, a base is, for example, (ii) a metal organic substance, including but not limited to, Li-organyl compounds, alkali metals like Na and K, or combinations thereof.

The base may comprise a solvent compatible with the respective base, e.g., with KOH, NaOH, LiOH, $Ca(OH)_2$, on the one hand, and, e.g., with Li-organyl compounds, alkali metals like Na and K, on the other hand. Examples of suitable solvents for the said bases, but not intended to be limited thereto, are water ($H_2O$) which is good for NaOH, KOH, LiOH, and $Ca(OH)_2$; hexane, cyclohexane for Li-organyl compounds like Bu-Li (butyl lithium), Me-Li (methyl lithium), and alkali metals like Na and K.

For example, the Method 1A process of the invention can be for the manufacture of the compound 1233xf (2-chloro-1,1,1-trifluoropropene), wherein the compound 1233xf is prepared in liquid phase under transfer catalysis reaction out of the compound 123 (2,2-dichloro-1,1,1-trifluoroethane). See for example, Embodiment Exemplification 3.

Method 1B:

Carbene generation in gas phase by high temperature thermolysis.

In the context of the present invention the carbene compound is formed, in a method 1B, by high temperature thermolysis of haloforms (R—$CHX_2$, wherein X denotes a halogen, e.g. especially chlorine, Cl).

The haloform employed in context of the present invention for generating a carbene of interest in the processes of manufacturing compounds according to the objects of the invention, is a trifluoroethane compound of the formula $CF_3$—$CHX_nY_{2-n}$, as defined above in the Summary of the Invention, for example, but not limited to, trifluoromethyl chloride.

Thermolysis, or thermal decomposition, is a chemical decomposition caused by heat. The decomposition temperature of a substance is the temperature at which the substance chemically decomposes. The reaction is usually endothermic as heat is required to break chemical bonds in the compound undergoing decomposition.

High temperature thermolysis, denotes a thermal decomposition at a temperature of about at least 400° C. For example, in the present invention the high temperature thermolysis is performed at a temperature in the range of about 400° C. to about 950° C. Preferably, the high temperature thermolysis is performed at a temperature in the range of about 500° C. to about 900° C. More preferably, the high temperature thermolysis is performed at a temperature in the range of about 700° C. to about 800° C.

For example, the Method 1B process of the invention can be for the manufacture of the compound 1233xf (2-chloro-1,1,1-trifluoropropene), wherein the compound 1233xf is prepared in a gas phase (vapor phase) reaction out of the compound 123 (2,2-dichloro-1,1,1-trifluoroethane), preferably in a continuous reaction, more preferably in a continuous reaction in a Monel-tube reactor. See for example, Embodiment Exemplification 1.

For example, the Method 1B process of the invention can be for the manufacture of the compound 1233xf (2-chloro-1,1,1-trifluoropropene), wherein the compound 1233xf is prepared in a gas phase (vapor phase) reaction out of the compound 123 (2,2-dichloro-1,1,1-trifluoroethane), preferably in a continuous reaction, more preferably in a continuous reaction in a quarz glass tube reactor. See for example, Embodiment Exemplification 2.

Method 2A and Method 2B (addition/elimination reaction):

The addition reaction in the second process step of manufacturing the compound 2,3,3,3-tetrafluoropropene (1234yf) according to the present invention can be performed by two methods:

Method 2A: Addition reaction of HF (hydrogen fluoride) and elimination of HCl (hydrogen chloride), both in liquid phase, and induced by Lewis acid; or Method 2B: Addition reaction of HF (hydrogen fluoride) and elimination of HCl (hydrogen chloride), both in gas phase (vapor-phase) in the presence of a fluorination and/or halogenation promoting catalyst.

For example, the chemistry to produce compound 1234yf out of compound 243db, according to Method 2A or 2B is shown in Scheme 1 above, in Step 2 (Addition/Elimination Reaction).

Details, as exemplification, for the Method 2A and Method 2B are given further below.

Method 2A, Liquid Phase Fluorination/Addition with HF (Lewis Acid):

The Method 2A can be performed in the liquid phase, by the addition reaction of HF (hydrogen fluoride) and elimination of HCl (hydrogen chloride), both in liquid phase, and wherein the addition reaction of HF and elimination of HCl is induced by a Lewis acid.

In the process according to the invention, the Lewis acid in step (c)-(i), as this step is defined in claim 1, is a metal halogenide, preferable a metal halogenide selected from the group consisting of $SbCl_5/SbF_5$, $TiCl_4/TiF_4$, $SnCl_4/SnF_4$, $FeCl_3/FeF_3$, $ZnCl_2/ZnF_2$, or is a halogenation promoting catalyst, preferably fluorination promoting catalyst, with Lewis acid properties.

Thus, suitable Lewis acids for the purpose of the present invention can also be a fluorination and/or halogenation promoting catalyst, especially wherein the catalyst is a fluorination (promoting) catalyst, as described further below.

For example, the Method 2A process of the invention can be for the manufacture of the compound 1234yf (2,3,3,3-tetrafluoropropene), wherein the compound 1234yf is prepared in liquid phase under transfer catalysis out of the compound 1233xf (2-chloro-1,1,1-trifluoropropene) by fluorination with anhydrous HF (hydrogen fluoride). The reaction can be performed in an autoclave, e.g., with PTFE in liner. The Lewis acid may be a fluorination and/or halogenation promoting catalyst, for example, $SbCl_xF_{5-x}$. See for example, Embodiment Exemplification 4.

Method 2B, Gas Phase (Vapor-Phase) Fluorination/Addition with HF (Catalyst):

The Method 2A can be performed in in gas phase (vapor-phase), by the addition reaction of HF (hydrogen fluoride) and elimination of HCl (hydrogen chloride), both in gas phase (vapor-phase), in the presence of a fluorination and/or halogenation promoting catalyst, especially wherein the catalyst is a fluorination (promoting) catalyst.

The gas phase (vapor-phase) fluorination process of the present invention is using gaseous hydrogen fluoride (HF) as the fluorination gas. Most preferably, the gaseous hydrogen fluoride (HF) as the fluorination gas is "100%" gaseous hydrogen fluoride (HF), meaning that the gaseous hydrogen fluoride (HF) used is essentially consisting of anhydrous gaseous hydrogen fluoride (anhydrous HF). The term "anhydrous" has the commonly applied technical meaning in the technical field of chemistry. Accordingly, a substance is "anhydrous" if it contains no water. Many processes in chemistry can be impeded by the presence of water. Therefore, it is important that water-free reagents and techniques are used. In practice, however, it is very difficult to achieve absolute dryness; anhydrous compounds gradually absorb water from the atmosphere so they must be stored and handled carefully to avoid such (re-)absorption of water. Techniques commonly known in the technical field of chemistry may be applied to prepare and to sustain gases, including gases of technical degree, essentially anhydrous.

The initial and/or preferred fluorination catalyst group of Cr-based catalysts used in the gas phase (vapor-phase) fluorination of the present invention, and used for preparing modifications of these Cr-based catalysts also used in the gas phase (vapor-phase) fluorination of the present invention, were prepared according to the recipe disclosed by Dow in 1955 in said U.S. Pat. No. 2,745,886. Therefore, disclosure of said U.S. Pat. No. 2,745,886 is incorporated herein for the purpose of the invention in its entirety.

The fluorination catalyst may be employed, for example in pelletized form, as granules, or in form of a fluorination catalyst supported on a carrier, e.g., inorganic carrier, resistant to hydrogen fluoride (HF). Catalyst carrier may be also in form of pellets or granules, or may be any other support structure suitable to carry a gas phase (vapor-phase) catalyst, resistant to hydrogen fluoride (HF).

The gas phase (vapor-phase) fluorination process of the present invention can be performed as a batch process or as a continuous process. The skilled person will readily understand that additional equipment has to be used, as applicable in a batch process or in a continuous process, respectively, e.g., inlets, outlets, pipes, measurement equipment for pressure, temperature, flow-measurement and the like, are employed as commonly known in the field of art, even if not specifically indicated herein below for reason of conciseness only.

In the process of the present invention particular focus preferably is put on a continuous gas phase (vapor-phase) fluorination process. Accordingly, also in case of a continuous gas phase (vapor-phase) fluorination step according to the present invention, the skilled person will readily understand that additional equipment has to be used for such continuous gas phase (vapor-phase) fluorination, e.g., inlets, outlets, pipes, measurement equipment for pressure, temperature, flow-measurement and the like, as applicable, are employed as commonly known in the field of art, even if not specifically indicated herein below for reason of conciseness only.

An exemplary apparatus for preparing, activating and/or re-activating the fluorination catalyst employed in the present invention, and/or for the gas phase (vapor-phase) fluorination process of the present invention, for example, is a reactor consisting out of a Monel-tube filled with catalyst pellets, a HF feeding system out of a stainless steel cylinder pressurized with $N_2$ (dosage from liquid phase over a Bronkhorst flow meter), a vaporizer operated at 180° C. for the feed to be halogenated, a condenser with a reservoir after the tube reactor still under slight overpressure, a scrubber just filled with water kept (cooled) at 25° C. and another scrubber filled with NaOH and a bubble counter at the exit allowing exhaust gas and the $N_2$ to exit.

For example, the Method 2B process of the invention is further exemplified below, for example, in the context of the Cr-based catalysts. The general gas-phase (vapor-phase) fluorination reaction with hydrogen fluoride (HF) as fluorination gas and fluorination catalyst based on chromium, for example, $Cr_2O_3$, is as further described herein below.

Methods with microreactor, applicable also to variant with coiled reactor:

According to a preferred embodiment of the present invention, the compound 1234yf (2,3,3,3-tetrafluoropropene) can also be prepared in a continuous manner out of the compound 123 (2,2-dichloro-1,1,1-trifluoroethane). Preferably, this reaction is performed in continuous manner. More preferably, the compound 1234yf (2,3,3,3-tetrafluoropropene) is prepared in a continuous manner out of the compound 123 (2,2-dichloro-1,1,1-trifluoroethane) in a two microreactor reaction. See for example, Embodiment Exemplification 5.

The, optionally intermediate, compound 243db (2,3-dichloro-1,1,1-trifluoropropane) produced in the first microreactor, optionally may be isolated and/or purified, and then be transferred into the second microreactor to be further reacted by fluorination with anhydrous HF (hydrogen fluoride). The Lewis acid may be a fluorination and/or halogenation promoting catalyst, for example, $SbCl_xF_{5-x}$, as used for example, also in Embodiment Exemplification 4.

The intermediate compound 243db (2,3-dichloro-1,1,1-trifluoropropane) produced in the first microreactor, optionally may be isolated and/or purified, and then be the final product.

Preferably, intermediate compound 243db (2,3-dichloro-1,1,1-trifluoropropane) produced in the first microreactor, as a crude compound 243db as obtained (e.g., not further purified), is transferred into the second microreactor to be further reacted by fluorination with anhydrous HF (hydrogen fluoride). See for example, Embodiment Exemplification 5. The Lewis acid may be a fluorination and/or halogenation promoting catalyst, for example, $SbCl_xF_{5-x}$, as used for example, also in Embodiment Exemplification 4.

In a variant of the present invention, see for example, Embodiment Exemplification 6, the compound 1234yf (2,3,3,3-tetrafluoropropene) can also be prepared out of the compound 125 (pentafluoroethane). Preferably, the reaction is performed in continuous manner. More preferably, the compound 1234yf (2,3,3,3-tetrafluoropropene) is prepared in a continuous manner out of the compound 125 (pentafluoroethane) in a microreactor reaction, such as the first microreactor according to Embodiment Exemplification 5.

In a further variant of the present invention, see for example, Embodiment Exemplification 7, the compound 1234yf (2,3,3,3-tetrafluoropropene) can also be prepared out of the compound 243db (2,3-dichloro-1,1,1-trifluoropropane). The reaction can be performed in the gas phase (vapor phase) by addition of HF (hydrogen fluoride), and elimination of HCl (hydrogen chloride). For example, the reaction is performed in two reaction zones (both zones as gas phase or vapor phase).

In the first reaction zone an intermediate carbene is generated out of the compound 243db, over a catalyst, and the intermediate carbene compound generated out of the compound 243db is further reacted by fluorination with anhydrous HF (hydrogen fluoride). Preferably, the catalyst is a chromium-based catalyst, preferably a Zn-doped chromium-based catalyst, e.g., Zn-doped chromium oxide ($Cr_2O_3$). The HCl formed in the first reaction zone, together with any residual HF, is stripped off in a cyclone, before the reaction product from the first zone enters the second reaction zone containing AlF3, preferably AlF3 in form of pellets. The reaction can be performed in a Monel-tube reactor, providing the two reaction zones. Preferably, the reaction can be performed in a continuous manner.

Fluorination catalyst, optionally with Lewis acid properties:

The processes of the invention employ a halogenation catalyst, preferably a fluorination catalyst. Halogenation is a chemical reaction that involves the addition of one or more halogens to a compound or material. The pathway and stoichiometry of halogenation depends on the structural features and functional groups of the organic substrate, as well as on the specific halogen. Inorganic compounds such as metals also undergo halogenation. Fluorination is a halogenation wherein F (fluorine) is the halogen introduced into a compound or material. Halogenation and/or fluorination are well known to those skilled in the art, as well as the halogenation catalysts and/or fluorination catalysts involved in these reactions. For example, the addition of halogens, e.g. chlorine and/or fluorine, to alkenes proceeds via intermediate halonium ions as an active species, wherein "halonium ion" in organic chemistry denotes any onium compound (ion) containing a halogen atom, e.g. herein in context of the invention a fluorine atom, carrying a positive charge.

Halogenation catalysts and/or fluorination catalysts are well known to those skilled in the field, and preferably in context of the invention, based on Sb, As, Bi, Al, Zn, Fe, Mg, Cr, Ru, Sn, Ti, Co, Ni, preferably on the basis of Sb.

The invention relates to a process, for example, wherein the catalyst is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst, wherein the fluorination catalyst is selected from the group consisting of Sb fluorination catalysts providing the active species $H_2F^+SbF^{6-}$.

The invention relates to a process, for example, wherein the halogenation catalyst is antimony pentachloride and/or antimony pentafluoride, preferably wherein the catalyst is antimony pentafluoride ($SbF_5$) and is prepared in an autoclave by reaction of $SbCl_5$ with HF, more preferably consisting of $SbF_5$ in HF which forms the active species $H_2F^+SbF^{6-}$, prior to reaction step (d) in the process according to any one of embodiments (1) to (3).

In particular, the invention pertains to a first process (process 1) for the manufacture of the compound 2,3,3,3-tetrafluoropropene (1234yf) comprising the steps of:

(a) providing the compound 243db (2,3-dichloro-1,1,1-trifluoropropane) as a starting material or intermediate material;

(b) providing (anhydrous) HF (hydrogen fluoride);

(c) mixing and reacting the compound 243db (2,3-dichloro-1,1,1-trifluoropropane) of (a) with the HF of (b), in a reactor, wherein (i) the reaction is performed by addition reaction of HF and elimination of HCl (hydrogen chloride), both in liquid phase, and induced by a Lewis acid; or (ii) the reaction is performed by addition reaction of HF and elimination of HCl (hydrogen chloride), both in gas phase (vapor-phase) in the presence of a halogenation promoting catalyst, preferably fluorination promoting catalyst;

(d) withdrawing the reaction mixture obtained in (c) from the said reactor in (c) to yield a 2,3,3,3-tetrafluoropropene (1234yf) comprising product, preferably a 2,3,3,3-tetrafluoropropene (1234yf) product;

(e) optionally withdrawing the HCl formed in the reactor in (c) as an effluent from reaction mixture obtained in (d); and (f) optionally purifying and/or isolating the 2,3,3,3-tetrafluoropropene (1234yf) product obtained in (d), or optionally in (e), to yield purified and/or isolated 2,3,3,3-tetrafluoropropene (1234yf).

In particular, the invention pertains to a second process (process 2) for the manufacture of the compound 243db (2,3-dichloro-1,1,1-trifluoropropane) comprising the steps of:

(a) providing the compound HCFC 123 (2,2-dichloro-1,1,1-trifluoroethane) as a starting material;

(b) generating a carbene (CF3-C(:)Cl) out of the compound HCFC 123 (2,2-dichloro-1,1,1-trifluoroethane) provided under (a), wherein
  (i) the carbene generation is performed in a liquid phase with a phase transfer catalyst and a base; or
  (ii) the carbene generation is performed in gas phase (vapor-phase) by high temperature thermolysis;

(c) mixing and reacting the carbene (CF3-C(:)Cl) formed in (b) with methyl chloride (CH$_3$Cl) and elimination of HCl (hydrogen chloride);

(d) withdrawing the reaction mixture obtained in (c) from the said reactor in (c) to yield a 243db (2,3-dichloro-1,1,1-trifluoropropane) comprising product, preferably a 243db (2,3-dichloro-1,1,1-trifluoropropane) product;

(e) optionally withdrawing the HCl formed in the reactor in (c) as an effluent from reaction mixture obtained in (d); and (f) optionally purifying and/or isolating the 243db (2,3-dichloro-1,1,1-trifluoropropane) product obtained in (d), or optionally in (e), to yield purified and/or isolated 243db (2,3-dichloro-1,1,1-trifluoropropane).

In particular, the invention pertains to a third process (process 3) for the manufacture of 2,3,3,3-tetrafluoropropene (1234yf) according to the first process of the invention, wherein in the step (a), as defined in the first process of the invention, the compound 243db (2,3-dichloro-1,1,1-trifluoropropane) provided as a starting material or intermediate material is obtained by the process for the manufacture of compound 243db (2,3-dichloro-1,1,1-trifluoropropane) as defined in the second process of the invention.

In particular, the invention pertains to a forth process (process 4) for the manufacture of the compound 1233xf (2-chloro-1,1,1-trifluoropropene) comprising the steps of:

(a) providing the compound HCFC 123 (2,2-dichloro-1,1,1-trifluoroethane) as a starting material;

(b) generating a carbene (CF3-C(:)Cl) out of the compound HCFC 123 (2,2-dichloro-1,1,1-trifluoroethane) provided under (a), wherein
  (i) the carbene generation is performed in a liquid phase with a phase transfer catalyst and a base; or
  (ii) the carbene generation is performed in gas phase (vapor-phase) by high temperature thermolysis;

(c) mixing and reacting the carbene (CF3-C(:)Cl) formed in (b) with methyl chloride (CH$_3$Cl) and elimination of HCl (hydrogen chloride), and further dehydrochlorination (—HCl);

(d) withdrawing the reaction mixture obtained in (c) from the said reactor in (c) to yield a 1233xf (2-chloro-1,1,1-trifluoropropene) comprising product, preferably a 1233xf (2-chloro-1,1,1-trifluoropropene) product;

(e) optionally withdrawing the HCl formed in the reactor in (c) as an effluent from reaction mixture obtained in (d); and (f) optionally purifying and/or isolating the 1233xf (2-chloro-1,1,1-trifluoropropene) product obtained in (d), or optionally in (e), to yield purified and/or isolated 1233xf (2-chloro-1,1,1-trifluoropropene).

In particular, the invention pertains to a fifth process (process 5) for the manufacture of the compound 2,3,3,3-tetrafluoropropene (1234yf) comprising the steps of:

(a) providing as a starting material (i) the compound 124 (2-chloro-1,1,1,2-tetrafluoroethane) and/or (ii) the compound 125 (pentafluoroethane);

(b) generating a carbene (CF3-C(:)F) out of (i) the compound 124 (2-chloro-1,1,1,2-tetrafluoroethane) and/or (ii) the compound 125 (pentafluoroethane) provided under (a), wherein
  (i) the carbene generation (CF3-C(:)F) is performed in a liquid phase with a phase transfer catalyst and a base; or
  (ii) the carbene generation (CF3-C(:)F) is performed in gas phase (vapor-phase) by high temperature thermolysis;

(c) mixing and reacting the carbene (CF3-C(:)F) formed in (b) with methyl chloride (CH$_3$Cl) and elimination of HCl (hydrogen chloride);

(d) withdrawing the reaction mixture obtained in (c) from the said reactor in (c) to yield a 2,3,3,3-tetrafluoropropene (1234yf) comprising product, preferably a 2,3,3,3-tetrafluoropropene (1234yf) product;

(e) optionally withdrawing (i) any or (ii) any HF, as formed in the carbene generation in (b), and the HCl formed in the reactor in (c), as an effluent from reaction mixture obtained in (d); and (f) optionally purifying and/or isolating the 2,3,3,3-tetrafluoropropene (1234yf) product obtained in (d), or optionally in (e), to yield purified and/or isolated 2,3,3,3-tetrafluoropropene (1234yf).

The invention comprises also a sixth process (process 6) according to any one of first or third process above, wherein the Lewis acid in step (c)-(i), as this step is defined in process 1, is a metal halogenide, preferable a metal halogenide selected from the group consisting of SbCl$_5$/SbF$_5$, TiCl$_4$/TiF$_4$, SnCl$_4$/SnF$_4$, FeCl$_3$/FeF$_3$, ZnCl$_2$/ZnF$_2$, or is a halogenation promoting catalyst, preferably fluorination promoting catalyst, with Lewis acid properties.

The invention comprises also a seventh process (process 7) according to any one of first or third process above, wherein the halogenation promoting catalyst, preferably fluorination promoting catalyst, in step (c)-(ii), as this step is defined in first process, or the halogenation promoting catalyst, preferably fluorination promoting catalyst, with Lewis acid properties, as defined in forth process, is a halogenation catalyst, preferably a fluorination catalyst, on the basis of Sb, As, Bi, Al, Zn, Fe, Mg, Cr, Ru, Sn, Ti, Co, Ni, preferably on the basis of Sb, more preferably a fluorination catalyst, wherein the Sb fluorination catalyst is selected from the group consisting of Sb fluorination catalysts providing the active species H$_2$F$^+$SbF$_6^-$.

The invention comprises also a eights process according to invention, wherein the halogenation catalyst is antimony pentachloride and/or antimony pentafluoride, preferably wherein the catalyst is antimony pentafluoride ($SbF_5$), and preferably is prepared in an autoclave by reaction of $SbCl_5$ with HF, more preferably consisting of $SbF_5$ in HF which forms the active species $H_2F^+SbF^{6-}$.

The invention comprises also a ninth process according to any one of process 2 to process 5, wherein the high temperature thermolysis in step (b)-(ii), as this step is defined in each of the processes 2 to 5, denotes a thermal decomposition performed at a temperature of about at least 400° C.; preferably wherein the high temperature thermolysis is performed at a temperature in the range of about 400° C. to about 950° C.; more preferably, the high temperature thermolysis is performed at a temperature in the range of about 500° C. to about 900° C.; still more preferably, the high temperature thermolysis is performed at a temperature in the range of about 700° C. to about 800° C.

The invention comprises also a tenth process according to any one of process 2 to process 5, wherein the phase transfer catalyst in step (b)-(i), as this step is defined in each of the processes 2 to 5, comprises or consists of a compound of at least one of the compound classes of a) linear or cyclic ammonium salts, b) heterocyclic ammonium salts, c) non-ionic phase transfer compounds, d) phosphonium salts, and combinations thereof.

The invention comprises also a process according to any one of process 2 to process 5, wherein the base in step (b)-(i), as this step is defined in each of the processes 2 to 5, comprises or consists of (i) an inorganic substance selected from the group consisting of KOH, NaOH, LiOH, $Ca(OH)_2$, or combinations thereof, or comprises or consists of (ii) a metal organic substance selected from the group consisting of Li-organyl compounds, alkali metals like Na and K, or combinations thereof.

The invention comprises also a process according to any one of the processes 1 and 3, wherein the halogenation promoting catalyst, preferably fluorination promoting catalyst, in step (c)-(ii), as this step is defined in process 1, is a fluorination catalyst is selected from the group consisting of $Cr_2O_3$ based catalyst, $MGF_2$ based catalyst, $SbCl_5/C$ based catalyst, and $FeCl_3/C$ based catalyst.

The invention comprises also a process, wherein the fluorination catalyst is selected from the group consisting of $MgF_2$ based catalyst, $SbCl_5/C$ based catalyst, and $FeCl_3/C$ based catalyst, and wherein the said catalyst is pre-fluorinated with hydrogen fluoride (HF).

The invention comprises also a process, wherein the fluorination catalyst is selected from the group $Cr_2O_3$ based catalyst.

The invention comprises also a process, wherein the $Cr_2O_3$ based catalyst is an activated and/or re-activated $Cr_2O_3$ based catalyst.

The invention comprises also a process according to, wherein the activated and/or re-activated $Cr_2O_3$ based catalyst is activated and/or re-activated by treatment with an oxygen containing gas; and/or wherein the $Cr_2O_3$ based catalyst, preferably the activated and/or re-activated $Cr_2O_3$ based catalyst, is pre-fluorinated with hydrogen fluoride (HF).

The invention comprises also a process, wherein the activated and/or re-activated $Cr_2O_3$ based catalyst is activated and/or re-activated by treatment with Zn dopant, preferably by treatment with $ZnCl_2$ as dopant, by treatment with Ni dopant, preferably by treatment with $NiCl_2$ as dopant.

The invention comprises also a process, wherein the activated and/or re-activated $Cr_2O_3$ based catalyst is activated and/or re-activated by treatment with Ni dopant, preferably by treatment with $NiCl_2$ as dopant, and wherein the said Ni dopant activated and/or re-activated $Cr_2O_3$ based catalyst is supported on $AlF_3$ as a carrier.

The invention comprises also a process, wherein the activated and/or re-activated $Cr_2O_3$ based catalyst is activated and/or re-activated by treatment with Mg dopant, preferably by treatment with Mg as dopant, and wherein the said Mg dopant activated and/or re-activated $Cr_2O_3$ based catalyst is additionally treated with carbon (C) to yield an activated and/or re-activated Cr—Mg—C fluorination catalyst.

The invention comprises also a process, wherein at least one reaction step, as defined in any of the steps (c)-(i) to (c)-(ii) in claim 1 or claim 3, or as defined in any of the steps (b)-(i) to (b)-(ii) in each of the processes 2 to 5, in the said reactors is performed in a continuous flow reactor; optionally wherein (i) the continuous flow reactor is a pipe-like continuous flow reactor, preferentially with minimal lateral dimensions of about >5 mm, more preferentially a pipe-like continuous flow reactor in coiled form (tube-like coiled reactor), or (ii) the continuous flow reactor is a microreactor, preferably with upper lateral dimensions of up to about ≤5 mm.

The invention comprises also a process, wherein the at least one reaction step in the said reactors is performed (i) in a continuous flow reactor that is a coiled continuous flow reactor; optionally wherein (i) the coiled continuous flow reactor is a coiled pipe-like continuous flow reactor, preferentially with minimal lateral dimensions of about >5 mm.

The invention comprises also a process, wherein the at least one reaction step in the said reactors is performed (ii) in a continuous flow reactor that is a microreactor, preferably with upper lateral dimensions of up to about ≤5 mm.

The invention comprises also a process, wherein the at least one reaction step is performed (ii) in a microreactor under one or more of the following conditions:
flow rate: of from about 10 ml/h up to about 400l/h;
temperature: of from about 30° C. up to about 150° C.;
pressure: of from about 5 bar up to about 50 bar;
residence time: of from about 1 minute up to about 60 minutes.

The invention comprises also a process, wherein at least one of the said continuous flow reactors, preferably at least one of the microreactors, is a SiC-continuous flow reactor, preferably independently is an SiC-microreactor.

PARTICULAR EMBODIMENTS OF THE INVENTION

Embodiment Exemplification 1

Continuous synthesis of 1233xf out of HCFC-123 in a Monel-tube reactor in gas phase, for example, according to following reaction scheme:

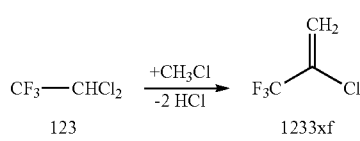

The reaction can be performed in a Monel tube (with desired dimension), diameter and length), electrically heated, $N_2$-flow during heating up, e.g., filled with about 1 cm Ni-fillings from company Raschig (Germany). The reactor temperature is e.g. at about 800° C., and the compound 123 feed can be controlled with a Bronkhorst flow meter over a vaporizer (operated e.g. at about 100° C.) is adjusted to desired g/h (desired mol/h) 123 feed, and another Bronkhorst flow meter is adjusted to an about equimolar to slight excess g/h (mol/h)chloromethane feed out of a gas cylinder into the Monel tube. The pressure is kept by a pressure valve at e.g. about 2 bar abs. The gas stream leaving the reactor tube is fed over a about 1 m cooled pipe (about +20° C.) of about 1 cm diameter into a water scrubber (operated at about room temperature) to absorb HCl and to hydrolyze little amounts of phosgene like side products. A GC/GC-MS analysis of the gas steam leaving the scrubber indicates a quantitative conversion of 123 and selectivity to 1233xf of about 96%. The gas steam after the scrubber is condensed into a stainless steel cylinder (fed inlet over a deep with deep) cooled to about −78° C. with $CO_2$/EtOH.

Embodiment Exemplification 2

Continuous synthesis of 1233xf out of HCFC-123 at about 800° C. in a quartz glass tube reactor in gas phase.

A quartz tube (with desired dimension), diameter and length) with electrical heating and a $N_2$-flow during heating up, filled with about 1 cm quartz glass fillings can be used. The reactor temperature is e.g. at about 800° C., the 123 feed can be controlled with a Bronkhorst flow meter over a vaporizer (operated e.g. at about 100° C.) is adjusted to desired g/h (desired mol/h) 123 feed, and another Bronkhorst flow meter is adjusted to an about equimolar to slight excess g/h (mol/h) chloromethane feed out of a gas cylinder. The pressure is kept by a pressure valve at e.g. about 1.2 bar abs. The gas stream leaving the reactor tube is fed over an about 1 m cooled pipe (about +25° C.) of about 1 cm diameter into a water scrubber to absorb HCl and to hydrolyze potential phosgene like side products and some unstable intermediates and phosgenes. A GC/GC-MS analysis of the gas steam leaving the scrubber indicates about 81% conversion of 123 and selectivity to 1233xf of about 89%. The gas stream after the scrubber is condensed into a stainless steel cylinder (fed inlet over a deep with deep) cooled to about −78° C. with $CO_2$/EtOH.

Embodiment Exemplification 3

Synthesis of 1233xf in liquid phase under phase transfer catalysis.

In a ml-sized Roth autoclave with deep pipe and gas outlet, a desired ml quantity of 123 (desired g, desired mol) is mixed with KOH pellets and a desired ml quantity deionized water together with a required quantity of TBAB (tetrabutylammoniumbomide, quantity required to achieve phase transfer condition) and the autoclave is closed. The autoclave is heated to e.g. about 80° C. Afterwards, a g-quantity (mol-quantity) liquid 123 (using a piston pump) and an about equimolar to slight excess g-quantity (mol-quantity) chloromethane (over a Bronkhorst flow meter out of a gas cylinder) is fed together over the deep pipe into the autoclave and the pressure was kept at e.g. about 4 bar abs. with a pressure valve installed at the gas outlet of the autoclave. The gas stream leaving the reactor tube is fed over an about 1 m cooled pipe (about +25° C.) of about 1 cm diameter into a water scrubber to absorb still some present HCl (most of the HCl remains in the autoclave). A GC/GC-MS analysis of the gas steam leaving the scrubber contains no 123 but mainly 1233xf. The gas stream after the scrubber is again condensed into a stainless steel cylinder (fed inlet over a deep pipe) cooled to about −78° C. with $CO_2$/EtOH.

Embodiment Exemplification 4

Fluorination of 1233xf in liquid phase to 1234yf, for example, according to following reaction scheme:

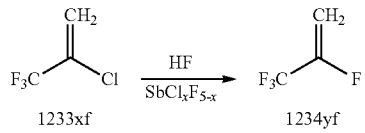

In a ml-sized Roth autoclave with PTFE in liner, a deep pipe and gas exit, a desired g-quantity (desired mol-quantity) of 1233xf is dissolved in a desired ml-quantity anhydrous HF fed out of a HF cylinder. Then $SbF_5$ (freshly prepared out of $SbCl_5$ (traces of Cl are not exchanged so the catalyst is $SbCl_xF_{5-x}$, preparation in another autoclave) is added. The autoclave with all the raw materials and the Sb is heated for e.g. about 1 h to e.g. about 95° C. (pressure raised to e.g. about 10 bar) and is slowly worked up after cooling down into ice water in a plastic washing bottle with deep pipe. The gas leaving the washing bottle is trapped into a stainless steel cylinder cooled to about −78° C. and consists out of 1234yf with traces of impurities only. Some unconverted 1233xf is found as second phase in the washing bottle. The isolated yield for 1234yf is about 76%, the 1233xf found back in the washing bottle indicated a conversion of about 79% and a selectivity to 1234yf of about 98%.

Embodiment Exemplification 5

Continuous preparation of 1234yf out of 123 in a two microreactor reaction sequence.

This process according to the invention is exemplified in FIG. 1, showing the synthesis of the compound 1234yf out of the compound 123 as the initial starting material, and performed as a reaction sequence in two microreactors.

1st step, for example, according to following reaction scheme:

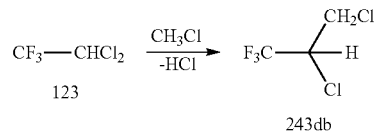

A first ml-sized microreactor made out of Nickel from company Innosyn BV (Geelen, Netherlands) for carbene generation (heated to about 700° C., pressure kept at about 12 bar abs. by a pressure valve) and a second ml-sized microreactor made out of SiC from Chemtrix were installed and operated in row. In a first step, HFC 243db is formed by $CF_3$—$CCl_2$:-carbene insertion (formed out of 123 which was fed as liquid into microreactor) into chloromethane. In comparison to the simple tube reactor out of Nickel or quartz glass, the residence time in this microreactor is carefully adjusted so as zero 1233xf is formed and quantitative conversion of compound 123 is achieved. After cooling the gas stream leaving microreactor 1 to about 0° C., over an about 100 cm coil (diameter about 1 cm) made out of Hastelloy C4, most of the formed HCl from first stage is stripped over a cyclone and liquid 243db is collected.

2nd step, for example, according to following reaction scheme:

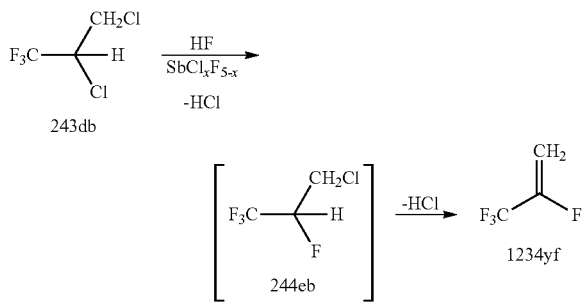

Crude HCFC 243db is not further purified and fed together as HF/Sb about molar 20:1 mixture (Sb)into the second microreactor heated to about 98° C., pressure kept at about 11 bar abs.

In microreactor 2, chlorine/fluorine exchange happens in situ followed by HCl-elimination catalyzed by the Lewis acid function of the Sb-catalyst. Another (not drawn) coil cooler operated at about 0° C. and another cyclone was applied after microreactor 2 to strip HCl. After the cyclone, the process stream entered a phase separator cooled to about-10° C. where a crude 1234yf gives the lower phase which is subjected to a continuous fine distillation. In a stainless steel column pure 1234yf at a transition temperature of about +35° C./about 10 bar abs. The upper phase of the separator is fed back into the HF/catalyst storage tank, about 5 mol-% (vs. Sb-concentration) of $F_2$ is added ($Cl_2$ also would be possible) into the stream to convert some formed low reactive $Sb^{III}$ back to the $Sb^{V}$ oxidation state (some deactivation of $Sb^{V} \rightarrow Sb^{III}$ happens during fluorination).

In this procedure, for example, a g-sized (e.g., about 3.27 mol) 123 per hour, and for example, an about equimolar to slight excess(e.g., about 166.6 g; e.g., about 3.3 mol) chloromethane per hour is reacted in two steps in about 92% yield and full 123 conversion to 1234yf. In seldom case of some traces of hydrolysable fluoride in the final distilled product, a further purification over NaF pellets can be applied.

Embodiment Exemplification 6

Synthesis of 1234yf out of 125 in microreactor, for example, according to following reaction scheme:

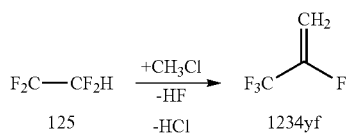

The installation is similar to that in Embodiment Exemplification 5 but only the first microreactor made out of Nickel is used.

Figure 2:
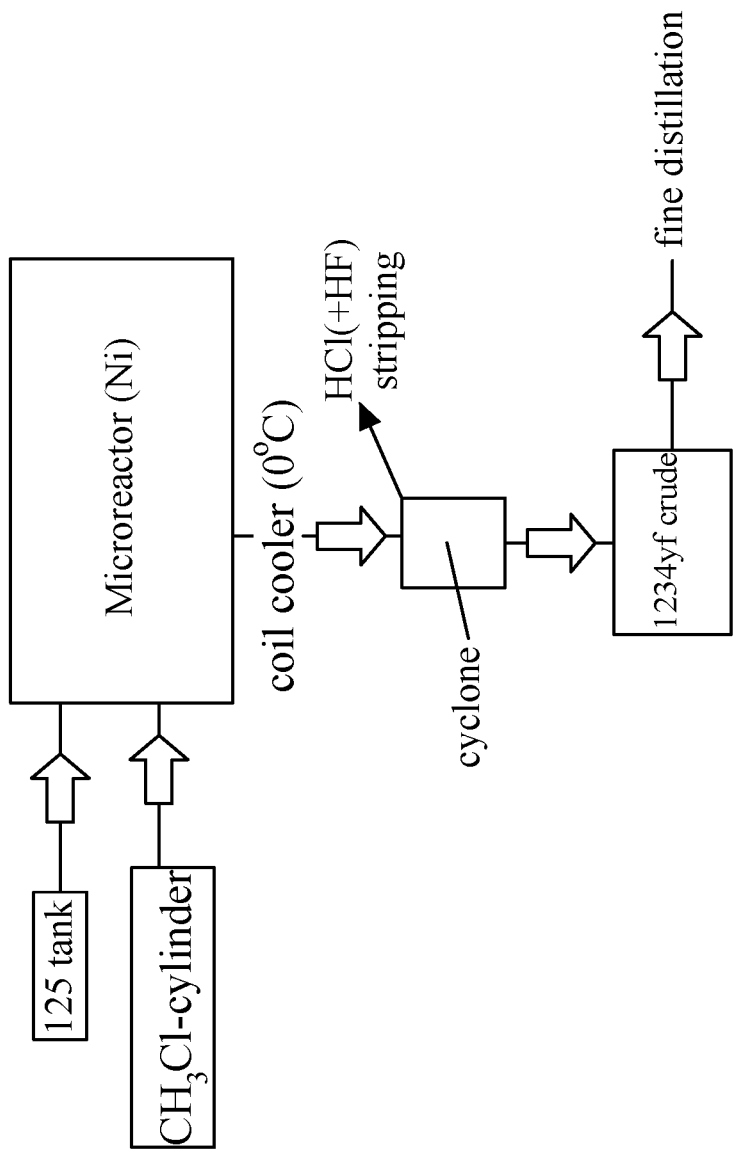
FIG. 2 shows an example embodiment of the process according to the invention and the synthesis of the compound 1234yf out of the compound 125 as the initial starting material, and performed as a reaction in a microreactor.

This process according to the invention is exemplified in FIG. 2, showing the synthesis of the compound 1234yf out of the compound 125 as the initial starting material, and performed as a reaction in a microreactor.

A g-size (e.g., about 360.1 g; e.g., about 3.0 mol) 125 per hour, and an about equimolar to slight excess g-size (e.g., about 161.6 g; e.g., about 3.2 mol) $CH_3Cl$ per hour is fed over Bronkhorst flow meters and out of stainless steel cylinders each into the microreactor kept at, e.g., about 12 bar abs. by a pressure valve. After the microreactor and the coil cooler (e.g., about 1 m length; e.g., about d=1 cm) operated at, e.g., about 0° C., some HF with most of the formed HCl is leaving over the cyclone. The product stream after the cyclone is all collected in a cooling trap kept at about −78° C. An analysis of the gas phase of a carefully hydrolyzed sample out of that cylinder showed an about 75% conversion of 125 and selectivity to 1234yf of about 98%. The stainless steel column as described in Embodiment Exemplification 5 is used for a fine distillation (at about 10 bar abs.) of material previously washed over ice water before distillation. The achieved 1234yf purity at a transition temperature of about 35° C. was about 99.9% (GC).

Embodiment Exemplification 7

Synthesis of 1234yf out of 243db in gas phase with Zn doped $Cr_2O_3$-catalyst over two reaction zones, for example, according to following reaction scheme:

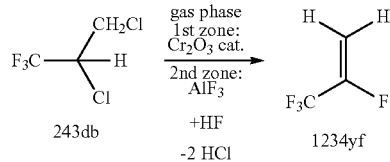

Apparatus: The 2 zone tube reactor system consists out of, for example, about 2×25 cm Monel-tube (for example, about diameter 5 cm). The first zone is filled with Zn doped $Cr_2O_3$ catalyst pellets. A HF feeding system is installed over a vaporizer and consists out of a stainless steel cylinder pressurized with $N_2$ (dosage from liquid phase over a Bronkhorst flow meter into the vaporizer). The vaporizer is operated at, for example, about 120° C. (needed for the 243db b.p. 77° C.). The zones are separated by a cyclone where almost all HCl together with most of the HF is stripped out before the material enters the second zone. The second zone (for example, about 25 cm) is filled with $AlF_3$ pellets (for example, about d=2 mm) prepared out of commercial AlF3 powder by pressing. The first zone is electrically heated to, for example, about 150° C., the second zone to, for example, about 350° C.

Recipe for the preparation of the catalysts (given quantities and measures are for example only, and may be easily modified by the person skilled in the art): Zn-doped $Cr_2O_3$ catalyst preparation: about 1 kg (about 19.2 mol) of chromia in form of granules of size about 0.5 to about 1.4 mm and surface of about 50 $m^2/g$ (Strem chemicals) was added to a solution of about 78.6 g (about 0.5769 mol) $ZnCl_2$ in about 1l distilled water and stirred for about 1 h at room temperature. Afterwards, the material was dried in vacuum (about 20 mbar/about 60° C.) until no weight loss could be observed resulting in particles of size about 0.5 to about 1.4 mm with about 3 wt.-% Zn. This catalyst was filled into the first zone of the reactor and pre-fluorinated about 2 h with an anhydrous HF stream until no water could be detected any more in the stream leaving the reactor. The AlF$_3$-pellets were just dried in N$_2$-stream at about 350° C. before usage.

A g-size (e.g., about 250 g; e.g., about 1.50 mol) 243db per hour is fed together with an about five times equimolar to slight excess-size (e.g., about 150 g; e.g., about 7.5 mol) anhydrous HF per hour over the vaporizer into zone 1 and after having passed a cyclone into zone 2. The pressure was kept at about 10 bar by a pressure valve after reactor 2, another valve at the exit of the cyclone (operated at about 21° C.) was adjusted to a material flow of about 3 l/minute into a scrubber system. The gas stream leaving reactor 2 was fed over another cyclone to strip HCl before it was collected into a cooling trap (at about −78° C.). All material collected in the cooling trap was carefully washed with ice water (washing bottle), the gas steam leaving the washing bottle indicated already a 1234yf crude material composition of about 98% besides some undefined % impurities. Isolated 1234yf is about 78% over the two steps.

The Process of the Invention (Monel-Tube Reactor):

An exemplary apparatus for preparing, activating and/or re-activating the fluorination catalyst employed in the present invention, and/or for the gas phase (vapor-phase) fluorination process of the present invention, for example, is a reactor consisting out of a Monel-tube filled with catalyst pellets, a HF feeding system out of a stainless steel cylinder pressurized with N$_2$ (dosage from liquid phase over a Bronkhorst flow meter), a vaporizer operated at 180° C. for the starting material feed, a condenser with a reservoir after the tube reactor still under slight overpressure, a scrubber just filled with water kept (cooled) at 25° C. and another scrubber filled with NaOH and a bubble counter at the exit allowing exhaust gas and the N$_2$ to exit.

For the gas phase (vapor-phase) fluorination process of the present invention, for example, the Monel tube (d=10 cm, volume around 6.5 l, electrically heated) is filled with a kg-scale quantity of the fluorination catalyst, for example at least 1 kg of the fluorination catalyst, preferably at least 2 kg, 3 kg, or 4 kg, more preferably at least 5 kg, or even at least 6 kg, 7 kg, 8 kg or 9 kg of the fluorination catalyst. The Monel tube is (electrically) heated to the reaction temperature of at least about 200° C., preferably of at least about 250° C., more preferably to a reaction temperature of about 280° C., and then the feed into the monel tube, of HF feed and starting material feed, was adjusted in relation to the employed kg-scale quantity of the fluorination catalyst, for example, based on 1 kg of the fluorination catalyst, the feed is adjusted to HF and starting material feed, both feeds fed over the vaporizer, which is operated at 180° C. for 1 h. Carefully hydrolyzed samples (see below), taken during the described gas phase (vapor-phase) fluorination process of the present invention from the fluorination product reservoir, showed almost quantitative conversion. The reaction time can be adjusted in relation to the employed quantity of fluorination catalyst on the one hand, and the quantity of HF feed and or starting material feed on the other hand.

It goes without saying that it is apparent to the person skilled in the art to also use any other reactor equipment suitable for catalytic gas phase reactions, fitted to be resistant to hydrogen fluoride (HF).

According to the vapor-phase fluorination process of the invention a reaction temperature is to be achieved and sustained at a vapor-phase reaction temperature in a range of from about 200° C. to about 300° C., preferably in a range of from about 250° C. to about 300° C., more preferably in a range of from about 270° C. to about 290° C.; and for example of about 280° C.

All materials, e.g., gas phase (vapor-phase) fluorination product, obtained in the gas phase (vapor-phase) fluorinations of the present invention leaving the reactors were collected by means of a condenser with a (product) reservoir. After having finished the gas phase (vapor-phase) fluorination, the collected gas phase (vapor-phase) fluorination product is worked up, by hydrolysis, by pouring the collected gas phase (vapor-phase) fluorination product very carefully into cooled water, preferably cooled water at a temperature of about 0° C. to about 10° C., more preferably cooled water at a temperature of about 0° C. to about 5° C. In a particular example, the gas phase (vapor-phase) fluorination product, obtained is carefully poured into ice water. The fluorinated product is further worked up by phase separation of the organic phase from the water phase, and optionally can be further purified by distillation of the organic phase at atmospheric pressure, to obtain the purified product.

The Cr-Based Catalysts:

The general gas-phase (vapor-phase) fluorination reaction with hydrogen fluoride (HF) as fluorination gas and fluorination catalyst based on chromium, for example, Cr$_2$O$_3$.

In the present invention the fluorination catalyst of the U.S. Pat. No. 2,745,886 (1955) is analogously used for the gas-phase (vapor-phase) fluorination reaction step with hydrogen fluoride (HF) as fluorination gas. Herein the hydrated chromium fluoride may be activated with oxygen as particularly described in the U.S. Pat. No. 2,745,886 (1955), and that the catalyst material so activated is very effective in catalyzing the vapor-phase fluorination reaction of the starting material and hydrogen fluoride (HF) as the fluorination gas. In fact, the catalysts are believed to be basic chromium fluorides, and more active than CrF$_3$. The said catalysts are also more effective in directing the course of the vapor-phase fluorination to greater conversions and yields of more highly fluorinated products, and at much lower temperatures, than has been achieved before.

In a particular embodiment of the present invention, the fluorination catalyst was prepared according to example 3 part B as described U.S. Pat. No. 2,745,886 starting with Cr$_2$O$_3$ (99% purity) and HF (anhydrous, 100%) giving CrF$_3$×3 H$_2$O, and, after adding 2 wt.-% graphite and formation of pellets, the catalyst was activated with oxygen.

In analogy to example 3 part B as described U.S. Pat. No. 2,745,886, the catalyst in accordance with the present invention was prepared by passing a stream of oxygen through a bed of 3/16 inch by 3/16 inch disc-shaped pellets containing 2 weight percent graphite prepared according to the following procedure:

A catalyst in accordance with the invention was prepared by reacting high purity chromium trioxide (CrO$_3$) with an excess of 70 weight percent hydrofluoric acid. The semi-crystalline bright green reaction product was heated in a drying oven at 80° C. to sensible dryness. This sensibly dry product, consisting preponderantly of α-CrF$_3$×3H$_2$O was ground to pass through a 10 mesh screen, admixed with 2 weight percent graphite, and was pressed into 3/16 inch by 3/16 inch disc-shaped pellets.

The dimensions of the catalyst bed and the conditions of the activation step were the same as described in example 3 of U.S. Pat. No. 2,745,886, except that oxygen was employed instead of air, e.g., according to the following procedure:

The catalyst pellets produced as described here-above were packed to a height of about 12 inches in the 2 inch nickel reaction tube as described in the examples of U.S. Pat. No. 2,745,886, or alternatively or preferably, into a Monel tube as described herein-above and employed in in the context of the present invention. The catalyst pellets were then activated by heating them to, and holding them for two hours at, 500° C. in a stream of oxygen. Of course, alternatively also air as described in example of U.S. Pat. No. 2,745,886 can be used.

The Cr-based catalysts prepared above are amorphous to X-ray diffraction analysis.

For example, the process of preparing a Cr-based fluorination catalysts for use in the vapor-phase process of the present invention can be performed such that the method of preparing a catalyst useful in promoting the fluorination by vapor-phase reaction with hydrogen fluoride, said method comprising heating a mixture of a major proportion of hydrated chromium fluoride and a minor proportion of chromium trioxide at a temperature above about 400° C. for a time sufficiently long to convert at least part of the hydrated chromium fluoride to a basic chromium fluoride.

For example, the process of preparing a Cr-based fluorination catalysts for use in the vapor-phase process of the present invention can be performed such that the method of preparing a catalyst useful in promoting the fluorination by vapor-phase reaction with hydrogen fluoride, said method consisting essentially of heating a hydrated chromium fluoride to a temperature in the range of from about 350° to 750° C. in the presence of oxygen.

For example, the process of preparing a Cr-based fluorination catalysts for use in the vapor-phase process of the present invention can be performed such that the method of preparing a catalyst useful in promoting the fluorination by vapor-phase reaction with hydrogen fluoride, said method consisting essentially of heating a hydrated chromium fluoride to. a temperature in the range of from about 350° C. to about 650° C., while passing a: stream of a gas comprising molecular oxygen there through for a time sufficiently long for a small though effective amount of oxygen to react therewith.

For example, the process of preparing a Cr-based fluorination catalysts for use in the vapor-phase process of the present invention can be performed such that in the said process the gas stream is oxygen.

For example, the process of preparing a Cr-based fluorination catalysts for use in the vapor-phase process of the present invention can be performed such that in the said process the gas stream is air.

For example, the process of preparing a Cr-based fluorination catalysts for use in the vapor-phase process of the present invention can be performed such that the said method is comprising heating a bed of $CrF_3 \times 3H_2O$ to an activation temperature in the range of from 350° to 650° C., while passing a stream of a gas comprising molecular oxygen there through, the flow of gas being maintained through said bed within said activation temperature range for a time sufficiently long to convert at least part of the hydrated chromium fluoride to a basic chromium fluoride.

For example, the process of preparing a Cr-based fluorination catalysts for use in the vapor-phase process of the present invention can be performed such that the said the $CrF_3 \times 3H_2O$ is the alpha hydrate.

Microreactor Process/Coiled Reactor Process:

The invention also may pertain to a process for the manufacture of a fluorinated compound according to any of the preceding processes, wherein the process is a continuous process, preferably wherein the continuous process is carried out in a microreactor. The disclosure herein, throughout the application, is also applicable to coiled reactor, e.g., a tube-like coiled reactor (e.g., a tube reactor which is in coiled form). Hence, except for reactor dimensions, the data contained herein for "microreactor" is also applicable to a coiled reactor, e.g., tube-like coiled reactor.

In general, the fluorination gas containing the hydrogen fluoride (HF) is fed into the microreactor in accordance with the required stoichiometry (sometimes with a slight excess) for the targeted fluorinated product and fluorination degree, and adapted to the reaction rate.

The invention may employ more than a single microreactor, i.e., the invention may employ two, three, four, five or more microreactors, for either extending the capacity or residence time, for example, to up to ten microreactors in parallel or four microreactors in series. If more than a single microreactor is employed, then the plurality of microreactors can be arranged either sequentially or in parallel, and if three or more microreactors are employed, these may be arranged sequentially, in parallel or both.

The invention is also very advantageous, in one embodiment wherein the direct fluorination of the invention optionally is performed in a continuous flow reactor system, or preferably in a microreactor system.

In an preferred embodiment the invention relates to a process for the manufacture of a fluorinated compound according to the invention, wherein the reaction is carried out in at least one step as a continuous processes, wherein the continuous process is performed in at least one continuous flow reactor with upper lateral dimensions of about ≤5 mm, or of about ≤4 mm, preferably in at least one microreactor;

more preferably wherein of the said steps at least (b2) the step of a fluorination reaction is a continuous process in at least one microreactor under one or more of the following conditions:

flow rate: of from about 10 ml/h up to about 400 l/h;
temperature: of from about 30° C. up to about 150° C.;
pressure: of from about 4 bar up to about 50 bar;
residence time: of from about 1 second, preferably from about 1 minute, up to about 60 minutes.

In another preferred embodiment the invention relates to such a process of preparing a compound according to the invention, wherein at least one of the said continuous flow reactors, preferably at least one of the microreactors, independently is a SiC-continuous flow reactor, preferably independently is a SiC-microreactor.

The Continuous Flow Reactors and Microreactors/Coiled Reactors:

In addition to the above, according to one aspect of the invention, also a plant engineering invention is provided, as used in the process invention and described herein, pertaining to the optional, and in some embodiments of the process invention, the process even preferred implementation in microreactors and/or in coiled reactors. Hence, except for reactor dimensions, the data contained herein for "microreactor" is also applicable to a coiled reactor, e.g., tube-like coiled reactor.

As to the term "microreactor": A "microreactor" or "microstructured reactor" or "microchannel reactor", in one embodiment of the invention, is a device in which chemical reactions take place in a confinement with typical lateral dimensions of about ≤1 mm; an example of a typical form of such confinement are microchannels. Generally, in the context of the invention, the term "microreactor": A "microreactor" or "microstructured reactor" or "microchannel reactor", denotes a device in which chemical reactions take place in a confinement with typical lateral dimensions of about ≤5 mm.

Microreactors are studied in the field of micro process engineering, together with other devices (such as micro heat exchangers) in which physical processes occur. The microreactor is usually a continuous flow reactor (contrast with/to a batch reactor). Microreactors offer many advantages over conventional scale reactors, including vast improvements in energy efficiency, reaction speed and yield, safety, reliability, scalability, on-site/on-demand production, and a much finer degree of process control.

Microreactors are used in "flow chemistry" to perform chemical reactions.

In flow chemistry, wherein often microreactors are used, a chemical reaction is run in a continuously flowing stream rather than in batch production. Batch production is a technique used in manufacturing, in which the object in question is created stage by stage over a series of workstations, and different batches of products are made. Together with job production (one-off production) and mass production (flow production or continuous production) it is one of the three main production methods. In contrast, in flow chemistry the chemical reaction is run in a continuously flowing stream, wherein pumps move fluid into a tube, and where tubes join one another, the fluids contact one another. If these fluids are reactive, a reaction takes place. Flow chemistry is a well-established technique for use at a large scale when manufacturing large quantities of a given material. However, the term has only been coined recently for its application on a laboratory scale.

Continuous flow reactors, e.g. such as used as microreactor, are typically tube like and manufactured from non-reactive materials, such known in the prior art and depending on the specific purpose and nature of possibly aggressive agents and/or reactants. Mixing methods include diffusion alone, e.g. if the diameter of the reactor is narrow, e.g. <1 mm, such as in microreactors, and static mixers. Continuous flow reactors allow good control over reaction conditions including heat transfer, time and mixing. The residence time of the reagents in the reactor, i.e. the amount of time that the reaction is heated or cooled, is calculated from the volume of the reactor and the flow rate through it: Residence time=Reactor Volume/Flow Rate. Therefore, to achieve a longer residence time, reagents can be pumped more slowly, just a larger volume reactor can be used and/or even several microreactors can be placed in series, optionally just having some cylinders in between for increasing residence time if necessary for completion of reaction steps. In this later case, cyclones after each microreactor help to let formed HCl to escape and to positively influence the reaction performance. Production rates can vary from milliliters per minute to liters per hour.

Some examples of flow reactors are spinning disk reactors (Colin Ramshaw); spinning tube reactors; multi-cell flow reactors; oscillatory flow reactors; microreactors; hex reactors; and aspirator reactors. In an aspirator reactor a pump propels one reagent, which causes a reactant to be sucked in. Also to be mentioned are plug flow reactors and tubular flow reactors.

In the present invention, in one embodiment it is particularly preferred to employ a microreactor.

In the use and processes according to the invention in a preferred embodiment the invention is using a microreactor. But it is to be noted in a more general embodiment of the invention, apart from the said preferred embodiment of the invention that is using a microreactor, any other, e.g. preferentially pipe-like, continuous flow reactor with upper lateral dimensions of up to about 1 cm, and as defined herein, can be employed. Thus, such a continuous flow reactor preferably with upper lateral dimensions of up to about ≤5 mm, or of about ≤4 mm, refers to a preferred embodiment of the invention, e.g. preferably to amicroreactor. Continuously operated series of STRs is another option, but less preferred than using a microreactor.

In the before said embodiments of the invention, the minimal lateral dimensions of the, e.g. preferentially pipe-like, continuous flow reactor can be about >5 mm; but is usually not exceeding about 1 cm. Thus, the lateral dimensions of the, e.g. preferentially pipe-like, continuous flow reactor can be in the range of from about >5 mm up to about 1 cm, and can be of any value therein between. For example, the lateral dimensions of the, e.g. preferentially pipe-like, continuous flow reactor can be about 5.1 mm, about 5.5 mm, about 6 mm, about 6.5 mm, about 7 mm, about 7.5 mm, about 8 mm, about 8.5 mm, about 9 mm, about 9.5 mm, and about 10 mm, or can be can be of any value intermediate between the said values.

In the before said embodiments of the invention using a microreactor preferentially the minimal lateral dimensions of the microreactor can be at least about 0.25 mm, and preferably at least about 0.5 mm; but the maximum lateral dimensions of the microreactor does not exceed about ≤5 mm. Thus, the lateral dimensions of the, e.g. preferential microreactor can be in the range of from about 0.25 mm up to about 5 mm, and preferably from about 0.5 mm up to about 5 mm, and can be of any value therein between. For example, the lateral dimensions of the preferential microreactor can be about 0.25 mm, about 0.3 mm, about 0.35 mm, about 0.4 mm, about 0.45 mm, and about 5 mm, or can be of any value intermediate between the said values.

As stated here before in the embodiments of the invention in its broadest meaning is employing, preferentially pipe-like, continuous flow reactor with upper lateral dimensions of up to about 1 cm. Such continuous flow reactor, for example is a plug flow reactor (PFR).

The plug flow reactor (PFR), sometimes called continuous tubular reactor, CTR, or piston flow reactors, is a reactor used to perform and describe chemical reactions in continuous, flowing systems of cylindrical geometry. The PFR reactor model is used to predict the behaviour of chemical reactors of such design, so that key reactor variables, such as the dimensions of the reactor, can be estimated.

Fluid going through a PFR may be modelled as flowing through the reactor as a series of infinitely thin coherent "plugs", each with a uniform composition, traveling in the axial direction of the reactor, with each plug having a different composition from the ones before and after it. The key assumption is that as a plug flows through a PFR, the fluid is perfectly mixed in the radial direction (i.e. in the lateral direction) but not in the axial direction (forwards or backwards).

Accordingly, the terms used herein to define the reactor type used in the context of the invention such like "continuous flow reactor", "plug flow reactor", "tubular reactor", "continuous flow reactor system", "plug flow reactor system", "tubular reactor system", "continuous flow system", "plug flow system", "tubular system" are synonymous to each other and interchangeably by each other.

The reactor or system may be arranged as a multitude of tubes, which may be, for example, linear, looped, meandering, circled, coiled, or combinations thereof. If coiled, for example, then the reactor or system is also called "coiled reactor" or "coiled system".

In the radial direction, i.e. in the lateral direction, such reactor or system may have an inner diameter or an inner cross-section dimension (i.e. radial dimension or lateral dimension, respectively) of up to about 1 cm. Thus, in an embodiment the lateral dimension of the reactor or system may be in the range of from about 0.25 mm up to about 1 cm, preferably of from about 0.5 mm up to about 1 cm, and more preferably of from about 1 mm up to about 1 cm.

In further embodiments the lateral dimension of the reactor or system may be in the range of from about >5 mm to about 1 cm, or of from about 5.1 mm to about 1 cm.

If the lateral dimension at maximum of up to about ≤5 mm, or of up to about ≤4 mm, then the reactor is called "microreactor". Thus, in still further microreactor embodiments the lateral dimension of the reactor or system may be in the range of from about 0.25 mm up to about ≤5 mm, preferably of from about 0.5 mm up to about ≤5 mm, and more preferably of from about 1 mm up to about ≤5 mm; or the lateral dimension of the reactor or system may be in the range of from about 0.25 mm up to about ≤4 mm, preferably of from about 0.5 mm up to about ≤4 mm, and more preferably of from about 1 mm up to about ≤4 mm.

In an alternative embodiment of the invention, it is also optionally desired to employ another continuous flow reactor than a microreactor, preferably if, for example, the (halogenation promoting, e.g. the halogenation or preferably the halogenation) catalyst composition used in the halogenation or fluorination tends to get viscous during reaction or is viscous already as a said catalyst as such. In such case, a continuous flow reactor, i.e. a device in which chemical reactions take place in a confinement with lower lateral dimensions of greater than that indicated above for a microreactor, i.e. of greater than about 1 mm, but wherein the upper lateral dimensions are about ≤4 mm. Accordingly, in this alternative embodiment of the invention, employing a continuous flow reactor, the term "continuous flow reactor" preferably denotes a device in which chemical reactions take place in a confinement with typical lateral dimensions of from about ≥1 mm up to about ≤4 mm. In such an embodiment of the invention it is particularly preferred to employ as a continuous flow reactor a plug flow reactor and/or a tubular flow reactor, with the said lateral dimensions. Also, in such an embodiment of the invention, as compared to the embodiment employing a microreactor, it is particularly preferred to employ higher flow rates in the continuous flow reactor, preferably in the plug flow reactor and/or a tubular flow reactor, with the said lateral dimensions. For example, such higher flow rates, are up to about 2 times higher, up to about 3 times higher, up to about 4 times higher, up to about 5 times higher, up to about 6 times higher, up to about 7 times higher, or any intermediate flow rate of from about ≥1 up to about ≤7 times higher, of from about ≥1 up to about ≤6 times higher, of from about ≥1 up to about ≤5 times higher, of from about ≥1 up to about ≤4 times higher, of from about ≥1 up to about ≤3 times higher, or of from about ≥1 up to about ≤2 times higher, each as compared to the typical flow rates indicated herein for a microreactor. Preferably, the said continuous flow reactor, more preferably the plug flow reactor and/or a tubular flow reactor, employed in this embodiment of the invention is configured with the construction materials as defined herein for the microreactors. For example, such construction materials are silicon carbide (SiC) and/or are alloys such as a highly corrosion resistant nickel-chromium-molybdenum-tungsten alloy, e.g. Hastelloy®, as described herein for the microreactors.

A very particular advantage of the present invention employing a microreactor, or a continuous flow reactor with the before said lateral dimensions, the number of separating steps can be reduced and simplified, and may be devoid of time and energy consuming, e.g. intermediate, distillation steps. Especially, it is a particular advantage of the present invention employing a microreactor, or a continuous flow reactor with the before said lateral dimensions, that for separating simply phase separation methods can be employed, and the non-consumed reaction components may be recycled into the process, or otherwise be used as a product itself, as applicable or desired.

In addition to the preferred embodiments of the present invention using a microreactor according to the invention, in addition or alternatively to using a microreactor, it is also possible to employ a plug flow reactor or a tubular flow reactor, respectively.

Plug flow reactor or tubular flow reactor, respectively, and their operation conditions, are well known to those skilled in the field.

Although the use of a continuous flow reactor with upper lateral dimensions of about ≤5 mm, or of about ≤4 mm, respectively, and in particular of a microreactor, is particularly preferred in the present invention, depending on the circumstances, it could be imagined that somebody dispenses with an microreactor, then of course with yield losses and higher residence time, higher temperature, and instead takes a plug flow reactor or turbulent flow reactor, respectively. However, this could have a potential advantage, taking note of the mentioned possibly disadvantageous yield losses, namely the advantage that the probability of possible blockages (tar particle formation by non-ideal driving style) could be reduced because the diameters of the tubes or channels of a plug flow reactor are greater than those of a microreactor.

The possibly allegeable disadvantage of this variant using a plug flow reactor or a tubular flow reactor, however, may also be seen only as subjective point of view, but on the other hand under certain process constraints in a region or at a production facility may still be appropriate, and loss of yields be considered of less importance or even being acceptable in view of other advantages or avoidance of constraints.

In the following, the invention is more particularly described in the context of using a microreactor. Preferentially, a microreactor used according to the invention is a ceramic continuous flow reactor, more preferably a SiC (silicon carbide) continuous flow reactor, and can be used for material production at a multi-to scale. Within integrated heat exchangers and SiC materials of construction, it gives optimal control of challenging flow chemistry application. The compact, modular construction of the flow production reactor enables, advantageously for: long term flexibility towards different process types; access to a range of production volumes (5 to 400l/h); intensified chemical production where space is limited; unrivalled chemical compatibility and thermal control.

Ceramic (SiC) microreactors, are e.g. advantageously diffusion bonded 3M SiC reactors, especially braze and metal free, provide for excellent heat and mass transfer, superior chemical compatibility, of FDA certified materials of construction, or of other drug regulatory authority (e.g. EMA) certified materials of construction. Silicon carbide (SiC), also known as carborundum, is a containing silicon and carbon, and is well known to those skilled in the art. For example, synthetic SiC powder is been mass-produced and processed for many technical applications.

For example, in the embodiments of the invention the objects are achieved by a method in which at least one reaction step takes place in a microreactor. Particularly, in preferred embodiments of the invention the objects are achieved by a method in which at least one reaction step takes place in a microreactor that is comprising or is made of SiC ("SiC-microreactor"), or in a microreactor that is comprising or is made of an alloy, e.g. such as Hastelloy C, as it is each defined herein after in more detail.

Thus, without being limited to, for example, in an embodiment of the invention the microreactor suitable for, preferably for industrial, production an "SiC-microreactor" that is comprising or is made of SiC (silicon carbide; e.g. SiC as offered by Dow Corning as Type G1SiC or by Chemtrix MR555 Plantrix), e.g. providing a production capacity of from about 5 up to about 400 kg per hour; or without being limited to, for example, in another embodiment of the invention the microreactor suitable for industrial production is comprising or is made of Hastelloy C, as offered by Ehrfeld. Such microreactors are particularly suitable for the, preferably industrial, production of fluorinated products according to the invention.

In order to meet both the mechanical and chemical demands placed on production scale flow reactors, Plantrixmodules are fabricated from 3M™SiC (Grade C). Produced using the patented 3M (EP 1637 271 B1 and foreign patents) diffusion bonding technology, the resulting monolithic reactors are hermetically sealed and are free from welding lines/joints and brazing agents. More technical information on the Chemtrix MR555 Plantrix can be found in the brochure "CHEMTRIX—Scalable Flow Chemistry—Technical Information Plantrix® MR555 Series, published by Chemtrix BV in 2017, which technical information is incorporated herein by reference in its entirety.

Apart from the before said example, in other embodiments of the invention, in general SiC from other manufactures, and as known to the skilled person, of course can be employed in the present invention.

Accordingly, in the present invention as microreactor also the Protrix® of by Chemtrix can be used. Protrix® is a modular, continuous flow reactor fabricated from 3M silicon carbide, offering superior chemical resistance and heat transfer. In order to meet both the mechanical and chemical demands placed on flow reactors, Protrix® modules are fabricated from 3M® SiC (Grade C). Produced using the patented 3M (EP 1 637 271 B and foreign patents) diffusion bonding technology, the resulting monolithic reactors are hermetically sealed and are free from welding lines/joints and brazing agents. This fabrication technique is a production method that gives solid SiC reactors (thermal expansion coefficient=$4.1 \times 10^{-6} K^{-1}$).

Designed for flow rates ranging from 0.2 to 20 ml/min and pressures up to 25 bar, Protrix® allows the user to develop continuous flow processes at the lab-scale, later transitioning to Plantrix® MR555 (×340 scale factor) for material production. The Protrix® reactor is a unique flow reactor with the following advantages: diffusion bonded 3M® SiC modules with integrated heat exchangers that offer unrivaled thermal control and superior chemical resistance; safe employment of extreme reaction conditions on a g scale in a standard fumehood; efficient, flexible production in terms of number of reagent inputs, capacity or reaction time. The general specifications for the Protrix® flow reactors are summarized as follows: possible reaction types are, e.g. A+B→P1+Q (or C)→P, wherein the terms "A", "B" and "C" represent educts, "P" and "P1" products, and "Q" quencher; throughput (ml/min) of from about 0.2 up to about 20; channel dimensions (mm) of 1×1 (pre-heat and mixer zone), 1.4×1.4 (residence channel); reagent feeds of 1 to 3; module dimensions (width×height) (mm) of 110×260; frame dimensions (width×height×length) (mm) approximately 400×300×250; number of modules/frame is one (minimum) up to four (max.). More technical information on the ChemtrixProtrix® reactor can be found in the brochure "CHEMTRIX—Scalable Flow Chemistry—Technical Information Protrix®, published by Chemtrix BV in 2017, which technical information is incorporated herein by reference in its entirety.

The Dow Corning as Type G1SiC microreactor, which is scalable for industrial production, and as well suitable for process development and small production can be characterized in terms of dimensions as follows: typical reactor size (length×width×height) of 88 cm×38 cm×72 cm; typical fluidic module size of 188 mm×162 mm. The features of the Dow Corning as Type G1SiC microreactor can be summarized as follows: outstanding mixing and heat exchange: patented HEART design; small internal volume; high residence time; highly flexible and multipurpose; high chemical durability which makes it suitable for high pH compounds and especially hydrofluoric acid; hybrid glass/SiC solution for construction material; seamless scale-up with other advanced-flow reactors. Typical specifications of the Dow Corning as Type G1SiC microreactor are as follows: flow rate of from about 30 ml/min up to about 200 ml/min; operating temperature in the range of from about −60° C. up to about 200° C., operating pressure up to about 18 barg ("barg" is a unit of gauge pressure, i.e. pressure in bars above ambient or atmospheric pressure); materials used are silicon carbide, PFA (perfluoroalkoxy alkanes), perfluoroelastomer; fluidic module of 10 ml internal volume; options: regulatory authority certifications, e.g. FDA or EMA, respectively. The reactor configuration of Dow Corning as Type G1SiC microreactor is characterized as multipurpose and configuration can be customized. Injection points may be added anywhere on the said reactor.

Hastelloy® C is an alloy represented by the formula NiCr21Mo14W, alternatively also known as "alloy 22" or "Hastelloy® C-22. The said alloy is well known as a highly corrosion resistant nickel-chromium-molybdenum-tungsten alloy and has excellent resistance to oxidizing reducing and mixed acids. The said alloy is used in flue gas desulphurization plants, in the chemical industry, environmental protection systems, waste incineration plants, sewage plants. Apart from the before said example, in other embodiments of the invention, in general nickel-chromium-molybdenum-tungsten alloy from other manufactures, and as known to the skilled person, of course can be employed in the present invention. A typical chemical composition (all in weight-%) of such nickel-chromium-molybdenum-tungsten alloy is, each percentage based on the total alloy composition as 100%: Ni (nickel) as the main component (balance) of at least about 51.0%, e.g. in a range of from about 51.0% to about 63.0%; Cr (chromium) in a range of from about 20.0 to about 22.5%, Mo (molybdenum) in a range of from about 12.5 to about 14.5%, W (tungsten or wolfram, respectively) in a range of from about 2.5 to about 3.5%; and Fe (iron) in an amount of up to about 6.0%, e.g. in a range of from about 1.0% to about 6.0%, preferably in a range of from about 1.5% to about 6.0%, more preferably in a range of from about 2.0% to about 6.0%. Optionally, the percentage based on the total alloy composition as 100%, Co (cobalt) can be present in the alloy in an amount of up to about 2.5%, e.g. in a range of from about 0.1% to about 2.5%. Optionally, the percentage based on the total alloy composition as 100%, V (vanadium) can be present in the alloy in an amount of up to about 0.35%, e.g. in a range of from about 0.1% to about 0,35%. Also, the percentage based on the total alloy composition as 100%, optionally low amounts (i.e. ≤0.1%) of other element traces, e.g. independently of C (carbon), Si (silicon), Mn (manganese), P (phosphor), and/or S (sulfur). In such case of low amounts (i.e. ≤0.1%) of other elements, the said elements e.g. of C (carbon), Si (silicon), Mn (manganese), P (phosphor), and/or S (sulfur), the percentage based on the total alloy composition as 100%, each independently can be present in an amount of up to about 0.1%, e.g. each independently in a range of from about 0.01 to about 0.1%, preferably each independently in an amount of up to about 0.08%, e.g. each independently in a range of from about 0.01 to about 0.08%. For example, said elements e.g. of C (carbon), Si (silicon), Mn (manganese), P (phosphor), and/or S (sulfur), the percentage based on the total alloy composition as 100%, each independently can be present in an amount of, each value as an about value: C≤0.01%, Si≤0.08%, Mn≤0.05%, P≤0.015%, S≤0.02%. Normally, no traceable amounts of any of the following elements are found in the alloy compositions indicated above: Nb (niobium), Ti (titanium), Al (aluminum), Cu (copper), N (nitrogen), and Ce (cerium).

Hastelloy® C-276 alloy was the first wrought, nickel-chromium-molybdenum material to alleviate concerns over welding (by virtue of extremely low carbon and silicon contents). As such, it was widely accepted in the chemical process and associated industries, and now has a 50-year-old track record of proven performance in a vast number of corrosive chemicals. Like other nickel alloys, it is ductile, easy to form and weld, and possesses exceptional resistance to stress corrosion cracking in chloride-bearing solutions (a form of degradation to which the austenitic stainless steels are prone). With its high chromium and molybdenum contents, it is able to withstand both oxidizing and non-oxidizing acids, and exhibits outstanding resistance to pitting and crevice attack in the presence of chlorides and other halides. The nominal composition in weight-% is, based on the total composition as 100%: Ni (nickel) 57% (balance); Co (cobalt) 2.5% (max.); Cr (chromium) 16%; Mo (molybdenum) 16%; Fe (iron) 5%; W (tungsten or wolfram, respectively) 4%; further components in lower amounts can be Mn (manganese) up to 1% (max.); V (vanadium) up to 0.35% (max.); Si (silicon) up to 0.08% (max.); C (carbon) 0.01 (max.); Cu (copper) up to 0.5% (max.).

In another embodiments of the invention, without being limited to, for example, the microreactor suitable for the said production, preferably for the said industrial production, is an SiC-microreactor that is comprising or is made only of SiC as the construction material (silicon carbide; e.g. SiC as offered by Dow Corning as Type G1SiC or by Chemtrix MR555 Plantrix), e.g. providing a production capacity of from about 5 up to about 400 kg per hour.

It is of course possible according to the invention to use one or more microreactors, preferably one or more SiC-microreactors, in the production, preferably in the industrial production, of the fluorinated products according to the invention. If more than one microreactor, preferably more than one SiC-microreactors, are used in the production, preferably in the industrial production, of the fluorinated products according to the invention, then these microreactors, preferably these SiC-microreactors, can be used in parallel and/or subsequent arrangements. For example, two, three, four, or more microreactors, preferably two, three, four, or more SiC-microreactors, can be used in parallel and/or subsequent arrangements.

For laboratory search, e.g. on applicable reaction and/or upscaling conditions, without being limited to, for example, as a microreactor the reactor type Plantrix of the company Chemtrix is suitable. Sometimes, if gaskets of a microreactor are made out of other material than HDPTFE, leakage might occur quite soon after short time of operation because of some swelling, so HDPTFE gaskets secure long operating time of microreactor and involved other equipment parts like settler and distillation columns.

For example, an industrial flow reactor ("IFR", e.g. Plantrix® MR555) comprises of SiC modules (e.g. 3M SiC) housed within a (non-wetted) stainless steel frame, through which connection of feed lines and service media are made using standard Swagelok fittings. The process fluids are heated or cooled within the modules using integrated heat exchangers, when used in conjunction with a service medium (thermal fluid or steam), and reacted in zig-zag or double zig-zag, meso-channel structures that are designed to give plug flow and have a high heat exchange capacity. A basic IFR (e.g. Plantrix® MR555) system comprises of one SiC module (e.g. 3M® SiC), a mixer ("MHRX") that affords access to A+B→P type reactions. Increasing the number of modules leads to increased reaction times and/or system productivity. The addition of a quench Q/C module extends reaction types to A+B→P1+Q (or C)→P and a blanking plate gives two temperature zones. Herein the terms "A", "B" and "C" represent educts, "P" and "P" products, and "Q" quencher.

Typical dimensions of an industrial flow reactor ("IFR", e.g. Plantrix® MR555) are, for example: channel dimensions in (mm) of 4×4 ("RX", mixer) and 5×5 (MRH-I/MRH-II; "MR" denotes residence module); module dimensions (width x height) of 200 mm×555 mm; frame dimensions (width x height) of 322 mm×811 mm. A typical throughput of an industrial flow reactor ("IFR", e.g. Plantrix® MR555) is, for example, in the range of from about 50 l/h to about 400 l/h. in addition, depending on fluid properties and process conditions used, the throughput of an industrial flow reactor ("IFR", e.g. Plantrix® MR555), for example, can also be >400 l/h. The residence modules can be placed in series in order to deliver the required reaction volume or productivity. The number of modules that can be placed in series depends on the fluid properties and targeted flow rate.

Typical operating or process conditions of an industrial flow reactor ("IFR", e.g. Plantrix® MR555) are, for example: temperature range of from about −30° C. to about 200° C.; temperature difference (service−process)≤70° C.; reagent feeds of 1 to 3; maximum operating pressure (service fluid) of about 5 bar at a temperature of about 200° C.; maximum operating pressure (process fluid) of about 25 bar at a temperature of about ≤200° C.

The following examples are intended to further illustrate the invention without limiting its scope.

EXAMPLES

Following compounds or intermediates are prepared according to this invention:

Example 1: Continuous Synthesis of 1233xf Out of HCFC-123 at 800° C. in a Monel-Tube Reactor in Gas Phase

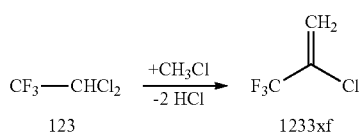

A Monel tube (d=10 cm, volume around 6.5 l, electrically heated, $N_2$-flow during heating up) was filled with 1 cm Ni-fillings from company Raschig (Germany). Once the reactor temperature reached 800° C., the 123 feed controlled with a Bronkhorst flow meter over a vaporizer (operated at 100° C.) was adjusted to 600 g/h (3.92 mol) and another Bronkhorst flow meter at 202 g/h (4.0 mol) chloromethane out of a gas cylinder into the Monel tube. The pressure was kept by a pressure valve at 2 bar abs. The gas stream leaving the reactor tube was fed over a 1 m cooled pipe (+20° C.) of 1 cm diameter into a water scrubber (operated at room temperature) to absorb HCl and to hydrolyze little amounts of phosgene like side products. A GC/GC-MS analysis of the gas steam leaving the scrubber indicated a quantitative conversion of 123 and selectivity to 1233xf of 96%. The gas steam after the scrubber was condensed into a stainless steel cylinder (fed inlet over a deep with deep) cooled to −78° C. with $CO_2$/EtOH.

Example 2: Continuous Synthesis of 1233xf Out of HCFC-123 at 800° C. in a Quarz Glass Tube Reactor in Gas Phase A quarz tube (d=10 cm, length 30 cm) with electrical heating and a $N_2$-flow during heating up) was filled with 1 cm quarz glass fillings. Once the reactor temperature reached 800° C., the 123 feed controlled with a Bronkhorst flow meter over a vaporizer (operated at 100° C.) was adjusted to 200 g/h (1.31 mol) and another Bronkhorst flow meter at 75.7 g (1.5 molmol/h) Chloromethane out of a gas cylinder. The pressure was kept by a pressure valve at 1.2 bar abs. The gas stream leaving the reactor tube was fed over a 1 m cooled pipe (+25° C.) of 1 cm diameter into a water scrubber to absorb HCl and to hydrolyze potential phosgene like side products and some unstable intermediates and phosgenes. A GC/GC-MS analysis of the gas steam leaving the scrubber indicated a 81% conversion of 123 and selectivity to 1233xf of 89%. The gas stream after the scrubber was condensed into a stainless steel cylinder (fed inlet over a deep with deep) cooled to −78° C. with $CO_2$/EtOH.

Example 3: Synthesis of 1233xf in Liquid Phase Under Phase Transfer Catalysis In a 250 ml Roth autoclave with deep pipe and gas outlet, 50 ml 123 (73 g, 0.48 mol) were mixed with 28 g KOH pellets from Aldrich and 30 ml deionized water together with 2 g TBAB (tetrabutylammoniumbomide, 0.006 mol) also from Aldrich and the autoclave was closed. The autoclave was heated to 80° C. Afterwards, 73 g (0.48 mol) liquid 123 (using a piston pump) and 30.29 g (0.6 mol) Chloromethane (over a Bronkhorst flow meter out of a gas cylinder) were fed together over the deep pipe into the autoclave and the pressure was kept at 4 bar abs. with a pressure valve installed at the gas outlet of the autoclave. The gas stream leaving the reactor tube was fed over a 1 m cooled pipe (+25° C.) of 1 cm diameter into a water scrubber to absorb still some present HCl (most of the HCl remained in the autoclave). A GC/GC-MS analysis of the gas steam leaving the scrubber contained no 123 but mainly 1233xf. The gas stream after the scrubber was again condensed into a stainless steel cylinder (fed inlet over a deep pipe) cooled to −78° C. with $CO_2$/EtOH.

Example 4: Fluorination of 1233xf in Liquid Phase to 1234yf

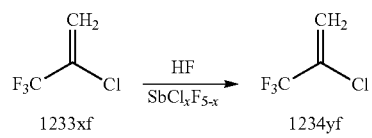

In a 250 ml Roth autoclave with PTFE in liner, a deep pipe and gas exit, 30 g (0.23 mol) 1233xf were dissolved in 50 ml anhydrous HF fed out of a HF cylinder. Then $SbF_5$ (freshly prepared out of $SbCl_5$ (traces of Cl are not exchanged so the catalyst is $SbC_xF_{5-x}$, preparation in another autoclave) were added. The autoclave with all the raw materials and the Sb was heated for 1 h to 95° C. (pressure raised to 10 bar) and was slowly worked up after cooling down into ice water in a plastic washing bottle with deep pipe. The gas leaving the washing bottle was trapped into a stainless steel cylinder cooled to −78° C. and consisted out of 1234yf with traces of impurities only. Some unconverted 1233xf was found as 2nd phase in the washing bottle. The isolated yield for 1234yf was 76%, the 1233xf found back in the washing bottle indicated a conversion of 79% and a selectivity to 1234yf of 98%.

Example 5: Continuous Preparation of 1234yf Out of 123 in a Two Microreactor Reaction Sequence 1st Step:

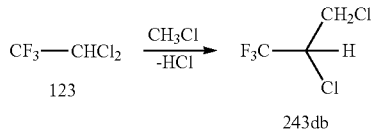

A first 30 ml microreactor made out of Nickel from company Innosyn BV (Geelen, Netherlands) for Carbene generation (heated to 700° C., pressure kept at 12 bar abs. by a pressure valve) and a 2nd 27 ml microreactor made out of SiC from Chemtrix were installed and operated in row. In a 1st step, HFC 243db is formed by $CF_3$—$CCl_2$:-Carbene insertion (formed out of 123 which was fed as liquid into microreactor) into Chloromethane. In comparison to the simple tube reactor out of Nickel or quartz glass, the residence time in this microreactor is carefully adjusted so as Zero 1233xf is formed and quantitative 123 conversion is achieved. After cooling the gas stream leaving microreactor 1 to 0° C. over a 100 cm coil (diameter 1 cm) made out of Hastelloy C4, most of the formed HCl from 1st stage is stripped over a Cyclone and liquid 243db is collected.

2nd Step:

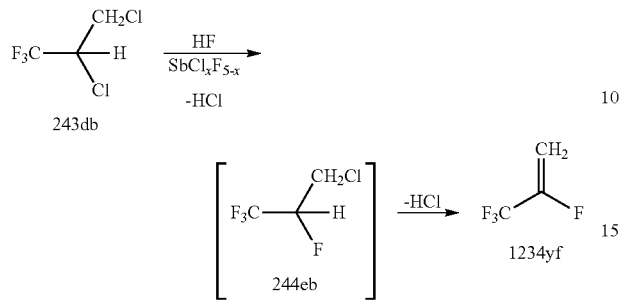

Crude HCFC 243db is not further purified and fed together as HF/Sb molar 20:1 mixture ($Sb^V$) into the 2nd microreactor heated to 98° C., pressure kept at 11 bar abs.

See FIG. 1 for the synthesis of compound 1234yf out of compound 123.

In microreactor 2, chlorine/fluorine exchange happened in situ followed by HCl-elimination catalyzed by the Lewis acid function of the Sb-catalyst. Another (not drawn) coil cooler operated at 0° C. and another cyclone was applied after microreactor 2 to strip HCl. After the cyclone, the process stream entered a phase separator cooled to −10° C. where a crude 1234yf gives the lower phase which was subjected to a continuous fine distillation. In a stainless steel column pure 1234yf at a transition temperature of +35° C./10 bar abs. The upper phase of the separator is fed back into the HF/catalyst storage tank, 5 mol-% (vs. Sb-concentration) of $F_2$ is added (Cl2 also would be possible) into the stream to convert some formed low reactive $Sb^{III}$ back to the $Sb^V$ oxidation state (some deactivation of $Sb^V \rightarrow Sb^{III}$ happens during fluorination).

In this procedure, 300 g (3.27 mol) 123 per hour and 166.6 g (3.3 mol) Chloromethane per hour were reacted after 2 steps in 92% yield and full 123 conversion to 1234yf. In seldom case of some traces of hydrolysable fluoride in the final distilled product, a further purification over NaF pellets was applied.

Example 6: Synthesis of 1234yf Out of 125 in Microreactor

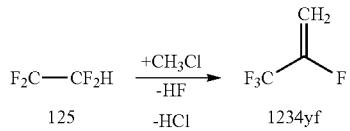

The installation is the same as in example 5 but only the 1$^{st}$ microreactor made out of Nickel is used.

See FIG. 2 for the synthesis of compound 1234yf out of compound 125.

The 360.1 g (3.0 mol) 125 per hour and 161.6 g (3.2 mol) $CH_3Cl$ per hour is fed over Bronkhorst flow meters and out of stainless steel cylinders each into the microreactor kept at 12 bar abs. by a pressure valve. After the microreactor and the coil cooler (1 m length, d=1 cm) operated at 0° C., some HF with most of the formed HCl is leaving over the Cyclone.

The product stream after the cyclone is all collected in a cooling trap kept at −78° C. An analysis of the gas phase of a carefully hydrolyzed sample out of that cylinder showed a 75% conversion of 125 and selectivity to 1234yf of 98%. The stainless steel column as described in example 5 was used for a fine distillation (at 10 bar abs.) of material previously washed over ice water before distillation. The achieved 1234yf purity at a transition temperature of 35° C. was 99.9% (GC).

Example 7: Synthesis of 1234yf Out of 243db in Gas Phase with Zn Doped $Cr_2O_3$-Catalyst Over Two Reaction Zones

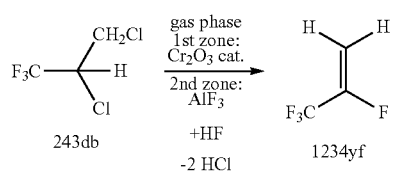

Apparatus: The 2 zone tube reactor system consists out of 2×25 cm Monel-tube (diameter 5 cm). The 1$^{st}$ zone was filled with Zn doped $Cr_2O_3$ catalyst pellets. A HF feeding system is installed over a vaporizer and consists out of a stainless steel cylinder pressurized with $N_2$ (dosage from liquid phase over a Bronkhorst flow meter into the vaporizer). The vaporizer is operated at 120° C. (needed for the 243db b.p. 77° C.). The zones are separated by a cyclone where almost all HCl together with most of the HF is stripped out before the material enters the 2$^{nd}$ zone. The 2$^{nd}$ zone (25 cm) is filled with $AlF_3$ pellets (d=2 mm) prepared out of commercial AlF3 powder by pressing. The 1$^{st}$ zone is electrically heated to 150° C., the 2$^{nd}$ zone to 350° C.

Recipe for the Preparation of the Catalysts:

Zn-doped $Cr_2O_3$ catalyst preparation: 1 kg (19.2 mol) of Chromia in form of granules of size 0.5-1.4 mm and surface of 50 m$^2$/g (Strem chemicals) was added to a solution of 78.6 g (0.5769 mol) $ZnCl_2$ in 1 l distilled water and stirred for 1 h at room temperature. Afterwards, the material was dried in vacuum (20 mbar/60° C.) until no weight loss could be observed resulting in particles of size 0.5-1.4 mm with 3 wt.-% Zn. This catalyst was filled into the 1$^{st}$ zone of the reactor and pre-fluorinated 2 h with an anhydrous HF stream until no water could be detected any more in the stream leaving the reactor. The $AlF_3$-pellets were just dried in $N_2$-stream at 350° C. before usage.

250 g (1.50 mol) 243db per hour was fed together with 150 g (7.5 mol) anhydrous HF per hour over the vaporizer into zone 1 and after having passed a cyclone into zone 2. The pressure was kept at 10 bar by a pressure valve after reactor 2, another valve at the exit of the cyclone (operated at 21° C.) was adjusted to a material flow of 3 l/minute into a scrubber system. The gas stream leaving reactor 2 was fed over another cyclone to strip HCl before it was collected into a cooling trap (−78° C.). All material collected in the cooling trap was carefully washed with ice water (washing bottle), the gas steam leaving the washing bottle indicated already a 1234yf crude material composition of 98% besides some undefined % impurities. Isolated 1234yf was 78% d. Th. over the 2 steps.

What is claimed is:

1. A process for the manufacture of the compound 2,3,3,3-tetrafluoropropene (1234yf) comprising the steps of:

(a) providing the compound 243db (2,3-dichloro-1,1,1-trifluoropropane) as a starting material or intermediate material;
(b) providing anhydrous HF (hydrogen fluoride);
(c) mixing and reacting the compound 243db (2,3-dichloro-1,1,1-trifluoropropane) of (a) with the HF of (b), in a reactor, wherein
a reaction is performed by addition reaction of HF and elimination of HCl (hydrogen chloride), both in liquid phase, and induced by a Lewis acid;
(d) withdrawing the reaction mixture obtained in (c) from the said reactor in (c) to yield a 2,3,3,3-tetrafluoropropene (1234yf) comprising product;
(e) withdrawing the HCl formed in the reactor in (c) as an effluent from reaction mixture obtained in (d); and
(f) purifying and/or isolating the 2,3,3,3-tetrafluoropropene (1234yf) product obtained in (d), or in (e), to yield purified and/or isolated 2,3,3,3-tetrafluoropropene (1234yf).

2. The process according to claim 1, wherein the Lewis acid is a metal halogenide, the metal halogenide being a metal halogenide selected from the group consisting of $SbCl_5/SbF_5$, $TiCl_4/TiF_4$, $SnCl_4/SnF_4$, $FeCl_3/FeF_3$, $ZnCl_2/ZnF_2$, or is a halogenation promoting catalyst, the halogenation promoting catalyst being fluorination promoting catalyst, with Lewis acid properties.

3. The process according to claim 1, wherein the said reactor is performed in a continuous flow reactor; the continuous flow reactor is a pipe continuous flow reactor or coiled continuous flow reactor with minimal lateral dimensions of about >5 mm.

4. The process according to claim 3, wherein at least one of the continuous flow reactors is a SiC-continuous flow reactor.

* * * * *